US006960079B2

(12) United States Patent
Brennan et al.

(10) Patent No.: US 6,960,079 B2
(45) Date of Patent: Nov. 1, 2005

(54) ORTHODONTIC ADHESIVES AND APPLIANCES INCLUDING AN ADHESIVE ON THE BASE OF THE APPLIANCE

(75) Inventors: Joan V. Brennan, Sierra Madre, CA (US); Sumita B. Mitra, West St. Paul, MN (US); Mark S. Schaberg, Lake Elmo, MN (US); Robert D. Kuehn, Eagan, MN (US); Joel D. Oxman, Minneapolis, MN (US); Darrell S. James, Covina, CA (US); Sharon M. Rozzi, Stillwater, MN (US); David K. Cinader, Yorba Linda, CA (US)

(73) Assignee: 3M Innovative Properties Company, St. Paul, MN (US)

( * ) Notice: Subject to any disclaimer, the term of this patent is extended or adjusted under 35 U.S.C. 154(b) by 101 days.

(21) Appl. No.: 10/126,505

(22) Filed: Apr. 18, 2002

(65) Prior Publication Data

US 2003/0198914 A1 Oct. 23, 2003

(51) Int. Cl.[7] .............................................. A61C 3/00
(52) U.S. Cl. ....................................................... 433/9
(58) Field of Search .............................. 433/8, 9, 23, 2; 206/368, 369, 63.5; 427/2.29; 428/317.7, 317.5, 355 R

(56) References Cited

U.S. PATENT DOCUMENTS

| | | |
|---|---|---|
| 3,655,605 A | 4/1972 | Smith et al. |
| 3,814,717 A | 6/1974 | Wilson et al. |
| 4,143,018 A | 3/1979 | Crisp et al. |
| 4,180,911 A * | 1/1980 | Bullock ........................ 433/9 |
| 4,209,434 A | 6/1980 | Wilson et al. |
| 4,360,605 A | 11/1982 | Schmitt et al. |
| 4,376,835 A | 3/1983 | Schmitt et al. |
| 4,503,169 A | 3/1985 | Randklev |
| 4,695,251 A | 9/1987 | Randklev |
| 4,936,775 A * | 6/1990 | Bennett ..................... 433/220 |
| 4,978,007 A | 12/1990 | Jacobs et al. |
| 5,015,180 A * | 5/1991 | Randklev ....................... 433/9 |
| 5,172,809 A | 12/1992 | Jacobs et al. |

(Continued)

FOREIGN PATENT DOCUMENTS

| | | |
|---|---|---|
| EP | 0 486 774 | 5/1992 |
| JP | HEI 11-139920 | 5/1999 |
| WO | WO 00/69393 | 11/2000 |
| WO | WO 02/30363 A2 | 4/2002 |

OTHER PUBLICATIONS

Chung et al., "Fluoride release and cariostatic ability of a compomer and a resin–modified glass ionomer cement used for orthodontic bonding," *Journal of Dentistry*, 1998, vol. 26, pp. 533–538.

Kirk–Othmer (Eds.), *Encyclopedia of Chemical Technology*, "Silica," 1997, 4th Ed., vol. 21, Title page, Publication page, Table of Contents and pp. 977–1032.

Macosko, *Rheology Principles, Measurements, and Applcations*, 1994, VCH Publishers, Inc., Title page and p. 92.

Millet et al., "A Comparative Clinical Trial of a Compomer and a Resin Adhesive for Orthodontic Bonding," *Angle Orthodontist*, Nov. 3, 2000, vol. 70, pp. 233–240.

Successful Use of Areosil ® Fumed Silica In Liquid Systems [online], Walsh & Associates, Inc., 1997 [retrieved on Jul. 7, 2002]. Retrieved from the Internet: <URL:http://www,walsh–assoc,com>. 2 pgs.

*Primary Examiner*—Todd E. Manahan
(74) *Attorney, Agent, or Firm*—James D. Christoff

(57) ABSTRACT

Orthodontic adhesives and packaged articles including an orthodontic appliance having a base for bonding the appliance to a tooth are disclosed. In the packaged articles, an adhesive is on the base of the appliance, and a container at least partially surrounds the orthodontic appliance having adhesive on the base thereof.

37 Claims, 1 Drawing Sheet

U.S. PATENT DOCUMENTS

| | | | |
|---|---|---|---|
| 5,183,403 A | * | 2/1993 | Masuhara et al. .............. 433/9 |
| 5,221,202 A | * | 6/1993 | James ........................... 433/9 |
| 5,328,363 A | | 7/1994 | Chester et al. |
| 5,332,429 A | | 7/1994 | Mitra et al. |
| 5,354,199 A | | 10/1994 | Jacobs et al. |
| 5,538,129 A | | 7/1996 | Chester et al. |
| 5,545,676 A | | 8/1996 | Palazzotto et al. |
| 5,552,177 A | | 9/1996 | Jacobs et al. |
| 5,575,645 A | | 11/1996 | Jacobs et al. |
| 5,698,020 A | | 12/1997 | Salz et al. |
| 5,846,075 A | | 12/1998 | Suh et al. |
| 6,050,815 A | * | 4/2000 | Adam et al. .................... 433/9 |
| 6,126,922 A | | 10/2000 | Rozzi et al. |
| 6,183,249 B1 | | 2/2001 | Brennan et al. |
| 6,331,080 B1 | | 12/2001 | Cole et al. |
| 6,444,725 B1 | | 9/2002 | Trom et al. |
| 6,528,555 B1 | * | 3/2003 | Nikutowski et al. ........ 523/116 |

\* cited by examiner

ORTHODONTIC ADHESIVES AND APPLIANCES INCLUDING AN ADHESIVE ON THE BASE OF THE APPLIANCE

BACKGROUND

Orthodontic treatment involves movement of malpositioned teeth to orthodontically correct positions. Tiny orthodontic appliances known as brackets are connected to exterior surfaces of the patient's teeth, and an archwire is placed in a slot of each bracket. The archwire forms a track to guide movement of the teeth to desired positions for correct occlusion. End sections of the archwire are often received in appliances known as buccal tubes that are fixed to the patient's molar teeth. In recent years it has become common practice to bond orthodontic appliances directly to the surface of the tooth.

For many years, it was common practice to apply orthodontic adhesive to the base of directly-bonded appliances immediately before the appliances were placed on the tooth. In some instances, a quantity of adhesive was dispensed onto a mixing pad or dispensing well and a small spatula or other hand instrument was then used to apply a small dab of adhesive to each appliance. In other instances, a quantity of adhesive was dispensed from a syringe directly onto the base of the appliance.

Adhesive precoated brackets are known and offer significant advantages to the orthodontist. Adhesive precoated brackets have a bonding base upon which the manufacturer may apply a precise quantity of adhesive such as a photocurable adhesive. When it is desired to mount the bracket on a tooth, the bracket is simply removed from the package and placed directly onto the tooth surface.

Photocurable adhesives offer advantages to orthodontic practitioners. In many types of orthodontic treatment, the exact position of the bracket on the corresponding tooth is highly important in order to facilitate moving the teeth to the desired positions without the need to place bends or twists in the archwire. As a consequence, the use of a photocurable orthodontic adhesive is highly beneficial in that the practitioner can take time to position the brackets in precise, appropriate locations. Once the practitioner is satisfied with the bracket positions, the curing light can be activated to quickly harden the adhesive and secure the brackets in place.

In addition to good handling properties and adequate adhesion, practitioners often desire that photocurable adhesives provide other desirable functional properties, including, for example, sustained fluoride release. In many applications, it is also desirable that the adhesive have adequate hydrophilicity or moisture tolerance, as indicated, for example, by the ability of the adhesive to absorb water or saliva.

Some attempts at precoating brackets with adhesives used adhesives that were more viscous (i.e., less fluid) than other available orthodontic adhesives. Higher viscosity was used to ensure that the adhesive retained its shape and did not separate or distort when the bracket was lifted from the package for use. However, some orthodontists prefer the use of less viscous (i.e., more fluid) adhesives in order to facilitate manipulation of the bracket before the adhesive is cured. For example, brackets with less viscous adhesives are relatively easy to slide along the tooth surface when an effort is made to align the bracket in a proper, precise orientation on the tooth before the adhesive is cured. However, the use of an adhesive with too low of a viscosity may be detrimental by causing the bracket to slip in the package or slip on the tooth (i.e., skating).

Orthodontic brackets precoated with adhesive are commonly sold with a flexible release substrate in contact with the adhesive. However, many release substrates are not suitable for use with all adhesives. For example, when soft, tacky, less viscous, hydrophilic adhesives are used, it has been found that a portion of the adhesive is sometimes left on the release substrate when an attempt is made to lift the appliance from the container and detach the adhesive from the release substrate. In those instances, sufficient adhesive may not remain on the bracket to provide adequate bond strength to retain the bracket on the tooth during the course of orthodontic treatment. Moreover, adhesives having a relatively low viscosity tend to slowly flow across the release substrate and from the space beneath the bracket over extended periods of time, creating bracket removal and/or liner release problems.

Additionally, when soft, tacky, less viscous adhesives are used with conventional adhesive precoated appliance packages, the shape of the adhesive may distort as the appliance is lifted from the container. In some instances, detaching the adhesive from the release substrate may alter the configuration of the adhesive, resulting in unsatisfactory direct bonding unless additional steps are undertaken to shift the adhesive by hand back to its original, pillow-like shape. For example, when lifting an appliance from the container, some of the adhesive may be shifted to one side of the appliance base, such that the opposite side of the base does not have a satisfactory amount of adhesive for bonding. If the appliance is secured to the tooth in such a manner that a void space is present between a portion of the base and the opposed tooth surface, the void space may result in premature, spontaneous debonding of the appliance from the tooth, a nuisance that is best avoided. Furthermore, in some instances the void space can establish a pocket that receives food and debris, facilitating the formation of caries.

In addition, there has been an increased interest in the use of adhesives that change from a noticeable color to a lack of color when curing. When uncured, such adhesives are easily observed, thus facilitating the clean-up of excess adhesive after the appliance has been positioned on the tooth surface. Once the adhesive has cured, the color is substantially eliminated, rendering the adhesive more difficult to see and, therefore, more aesthetic during the course of treatment.

Presently, there is a need in the art for precoated orthodontic appliances, wherein the adhesive provides a balance of properties and characteristics that are desired by the practitioner.

SUMMARY OF THE INVENTION

In one aspect, the present invention provides a packaged article including an orthodontic appliance. The orthodontic appliance has a base for bonding the appliance to a tooth, and an adhesive on the base of the appliance. In one embodiment, the adhesive includes a polymerizable component, a fluoride-releasing material, a hydrophilic component, a hardener, an acidic component, and a filler including a fumed silica having a surface area of at least about 70 $m^2/g$. A container at least partially surrounds the orthodontic appliance having adhesive on the base thereof. Preferably, the adhesive has a static yield stress at 28° C. of at least about 7000 $dynes/cm^2$. Preferably, the adhesive has a flow-out value of no greater than about 0.4 millimeters (mm) after one week at 40° C., wherein flow-out value is a measure of the tendency of an adhesive to flow on a liner as described herein. Preferably, the fumed silica has a surface area of about 70 $m^2/g$ to about 1000 $m^2/g$, more preferably about 90 m²/g to about 500 m²/g, and most preferably about 100 m²/g to about 150 m²/g. Optionally, the packaged article may be provided in a kit that includes, for example, instructions for using the orthodontic appliance.

In another aspect, the present invention provides a packaged article including an orthodontic appliance. The orthodontic appliance has a base for bonding the appliance to a tooth, and an adhesive on the base of the appliance. In one embodiment, the adhesive includes a polymerizable component, a fluoride-releasing material, a hydrophilic component, a hardener, an acidic component, a filler, and a photobleachable dye. Preferably, the hardener includes a sensitizing compound different from the photobleachable dye. The adhesive has an initial color prior to exposure to actinic radiation and a final color subsequent to exposure to actinic radiation, with the initial color being different than the final color. A container at least partially surrounds the orthodontic appliance having adhesive on the base thereof. Preferably, the filler includes fumed silica having a surface area of at least about 70 m²/g. Optionally, the packaged article may be provided in a kit that includes, for example, instructions for using the orthodontic appliance.

In another aspect, the present invention provides a method of bonding an orthodontic appliance to a tooth. In one embodiment, the method includes providing a packaged article including an orthodontic appliance having a base for bonding the appliance to a tooth, an adhesive on the base of the appliance, and a container at least partially surrounding the orthodontic appliance having adhesive on the base thereof. The adhesive includes a polymerizable component, a fluoride-releasing material, a hydrophilic component, a hardener, an acidic component, and a filler including fumed silica having a surface area of at least about 70 m²/g; removing the orthodontic appliance having adhesive on the base thereof from the container; applying the base of the appliance to the tooth surface; and exposing the adhesive to actinic radiation.

In another aspect, the present invention provides a method of bonding an orthodontic appliance to a tooth. In one embodiment, the method includes providing a packaged article including an orthodontic appliance having a base for bonding the appliance to a tooth, an adhesive on the base of the appliance, and a container at least partially surrounding the orthodontic appliance having adhesive on the base thereof, wherein the adhesive includes a polymerizable component, a fluoride-releasing material, a hydrophilic component, a hardener, an acidic component, a filler, and a photobleachable dye, and wherein the adhesive has an initial color prior to exposure to actinic radiation and a final color subsequent to exposure to actinic radiation, the initial color being different than the final color; removing the orthodontic appliance having adhesive on the base thereof from the container; applying the base of the appliance to the tooth surface; and exposing the adhesive to actinic radiation. Preferably, the hardener includes a sensitizing compound different from the photobleachable dye.

In another aspect, the present invention provides a packaged adhesive including an adhesive and a release substrate including a surface in contact with the adhesive. The adhesive includes a polymerizable component, a fluoride-releasing material, a hydrophilic component, a hardener, an acidic component, and a filler including a fumed silica having a surface area of at least about 70 m²/g, wherein the adhesive has a static yield stress at 28° C. of at least about 7000 dynes/cm² and a flow-out value of no greater than about 0.4 millimeters after one week at 40° C.

In another aspect, the present invention provides a packaged adhesive including an adhesive and a release substrate including a surface in contact with the adhesive. The adhesive includes a polymerizable component, a fluoride-releasing material, a hydrophilic component, a hardener, an acidic component, a filler, and a photobleachable dye, wherein the adhesive has an initial color prior to exposure to actinic radiation and a final color subsequent to exposure to actinic radiation, the initial color being different than the final color, and wherein the adhesive has a static yield stress at 28° C. of at least about 7000 dynes/cm². Preferably, the hardener includes a sensitizing compound different from the photobleachable dye.

Definitions

As used herein, "orthodontic appliance" refers to any device intended to be bonded to the teeth, including, but not limited to, orthodontic brackets, buccal tubes, lingual buttons, and cleats. Thus, the term "orthodontic appliance" encompasses orthodontic bands. The appliance has a base for receiving adhesive and it can be made of metal, plastic, ceramic, and combinations thereof As used herein, "hardenable" is descriptive of a material that can be cured or solidified, for example, by heating to remove solvent, heating to cause polymerization, chemical cross-linking, radiation-induced polymerization, or crosslinking.

As used herein, "hardener" means a system that initiates hardening of a resin. A hardener may include, for example, a polymerization initiator.

As used herein, "photobleachable" refers to loss of color upon exposure to actinic radiation.

As used herein, "filler" means a particulate material (e.g., an inorganic oxide) in dry powder form capable of being dispersed in a resin. For example, a dental composite preferably includes a powder dispersed in a resin.

As used herein, the term "silica" refers to the compound silicon dioxide. See Kirk-Othmer Encyclopedia of Chemical Technology, 4th Ed., Vol. 21, pp. 977–1032 (1977).

As used herein, the term "amorphous silica" refers to silica that does not have a crystalline structure as defined by x-ray diffraction measurements. Examples of amorphous silica include silica sols, silica gels, precipitated silica, and pyrogenic silica.

As used herein, the terms "pyrogenic silica" and "fumed silica" are used interchangeably and refer to amorphous silicas formed in the vapor phase. Pyrogenic silica may contain, for example, a few hundred primary particles fused into branched-chain, three-dimensional aggregates. Examples of pyrogenic silica include products available under the trade designations AEROSIL OX-50, AEROSIL-130, AEROSIL-150, AEROSIL-200, and AEROSIL R-972 available from DeGussa AG, (Hanau, Germany) and CAB-O-SIL M5 and CAB-O-SIL TS720 available from Cabot Corp. (Boston, Mass.).

As used herein, "base filler" refers to fillers other than fumed silica fillers. Base fillers include, for example, non-reactive fillers (e.g., quartz fillers), reactive fillers (e.g., fluoroaluminosilicate glass), and combinations thereof.

As used herein, "silane treated" means that the surface of a particle has been modified by application of a silane (e.g., dichlorodimethylsilane). Optionally, the silane may be a coupling agent that includes a reactive functionality (e.g., γ-methacryloxypropyltrimethoxysilane, A174).

As used herein, "aggregate length" means the longest dimension of the aggregate. As used herein, "aggregate" is descriptive of strongly associated primary particles often bound together by, for example, by residual chemical treatment, covalent chemical bonds, ionic chemical bonds, or hydrogen bonds.

As used herein, "slump" refers to the phenomenon of flow under the force of gravity. It is desirable that orthodontic adhesives do not slump because after they are placed in the mouth, the practitioner wants the imparted shape to remain unchanged until the materials are cured. It is also preferable that the adhesive can support the weight of the appliance without slumping. Slumping can lead to bracket drift and skating of the adhesive coated bracket on the tooth. Materials with a sufficiently high yield stress will not slump; that is, they will not flow under the stress of gravity. The yield stress of a material is the minimum stress required to cause the material to flow, and is described in Rheology Principles, Measurements, and Applications, C. W. Macosko, VCH Publishers, Inc., New York, 1994, p. 92. If the stress due to gravity is below the yield stress of the material, then the material will not flow. The stress due to gravity will depend on the mass of the adhesive being placed and the shape. It is desirable that the yield stress of an orthodontic adhesive be sufficiently high that the material does not slump in all types and sizes of uses. Preferably, the yield stress of an orthodontic adhesive will be sufficiently high that the material does not substantially slump when supporting a bracket on top of the adhesive. If the adhesive does flow out from underneath the bracket, preferably it will remain on a release substrate when the bracket is removed.

In certain applications of orthodontic adhesives, it is desirable that the pre-cured adhesive be preapplied (e.g., with a syringe) to an orthodontic appliance and the resulting adhesive precoated appliance packaged for later use by a practitioner. Alternatively, the adhesive can be preapplied to a release substrate and then packaged for later use by a practitioner to adhere an orthodontic appliance to a tooth. In both cases, it is critical that the packaged adhesive (whether applied on an appliance or a release substrate) does not slump over time. For certain embodiments, it is required that the preapplied (or precoated) adhesive does not slump under typical package storage and shipping conditions, for example, storage for up to 6 months, preferably for up to about 1 year, and more preferably for up to about 3 years. Generally storage would be expected to be at or below ambient temperature (i.e., room temperature), however, in some cases, storage and shipping conditions could be at greater than ambient temperature.

In order to determine or help predict the tendency of a packaged adhesive to slump over time, the adhesive can be evaluated for adhesive/bracket flow-out (or "flow-out") and/or adhesive/bracket vertical slip (or "slip") according to the test methods described herein. Briefly, flow-out measures the tendency over time of an adhesive to flow outwardly on a horizontally mounted release substrate beneath an orthodontic bracket; and slip measures the tendency of an adhesive-coated bracket vertically mounted on a release substrate to slip downward over time. For both measurements, it is preferable that the flow-out (after one week at 40° C.) and slip values are less than about 0.4 mm, more preferable less than about 0.25 mm, and most preferable 0 (zero). Flow-out or slip values greater than about 0.4 mm are readily apparent to the naked eye and can lead to significant problems during storage and/or shipping of the packaged adhesive. Such problems can include, for example, shape distortion of the adhesive on a release liner or, more seriously, separation of an orthodontic appliance from the adhesive when the appliance is removed from the package.

For such adhesive-coated, packaged articles of the present invention, it is preferable that the adhesive have a static yield stress at 28° C. of about 7000 dynes/cm$^2$ to about 100,000 dynes/cm$^2$; and have a steady state viscosity at 28° C. of about $3\times10^2$ Pascal-seconds (Pa-s) to about $7\times10^4$ Pa-s.

As used herein, the term "(meth)acrylate" is a shorthand reference to acrylate, methacrylate, or combinations thereof, and "(meth)acrylic" is a shorthand reference to acrylic, methacrylic, or combinations thereof.

As used herein, the chemical term "group" allows for substitution.

As used herein, "a" or "an" means one or more.

DETAILED DESCRIPTION OF THE PREFERRED EMBODIMENTS

Figure 1:
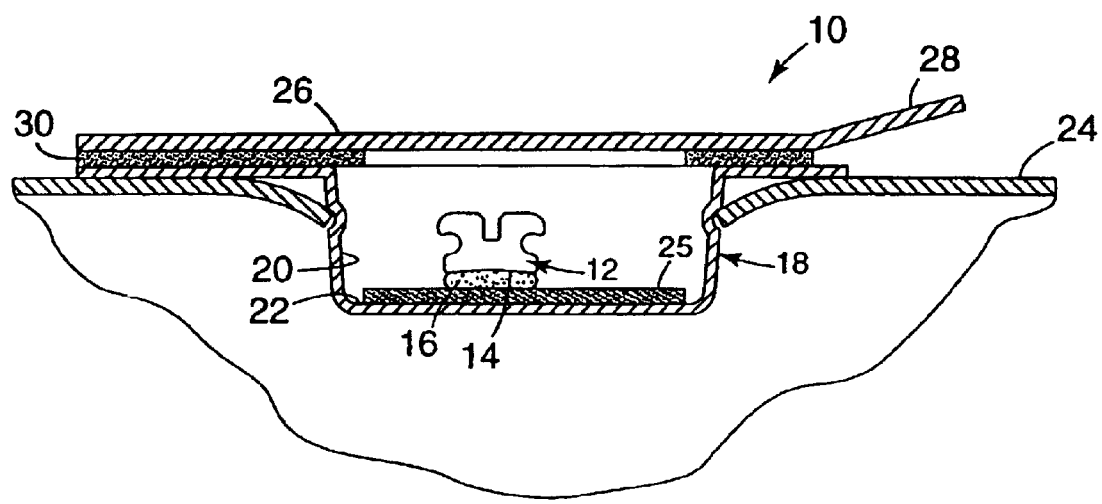
FIG. 1 is a fragmentary, side cross-sectional view of a packaged article according to one embodiment of the present invention.

In one embodiment, referring to FIG. 1, the present invention provides packaged article 10 including an orthodontic appliance such as bracket 12. The bracket 12 has a base 14 for directly bonding the bracket 12 to a patient's tooth structure. An adhesive 16 extends across the base 14 of the bracket 12. The bracket 12 and the adhesive 16 are at least partially surrounded by a container 18. The exemplary container 18 illustrated in FIG. 1 includes an integrally-molded body with internal wall portions that define a recess or well 20. The well 20 includes side walls and a bottom 22. As an additional option, the side walls of the well 20 include horizontally extending recesses for engagement with edge structure of carrier 24. Additional information regarding a suitable carrier 24 is set out in U.S. Pat. No. 5,328,363 (Chester et al.). Preferably, the bottom 22 of the well 20 includes a release substrate 25. Preferably, the article 10 also includes a cover 26 with a tab 28, with the cover 28 being connected to the container 18 by, for example, adhesive 30.

Figure 2:
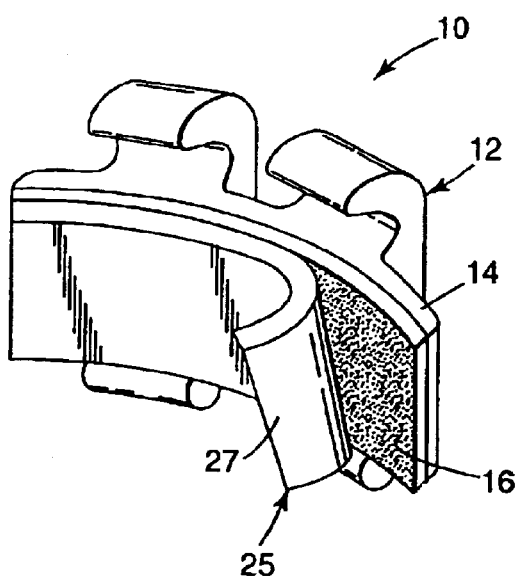
FIG. 2 is a perspective view of an orthodontic appliance according to another embodiment of the present invention.

In another embodiment, referring to FIG. 2, the present invention provides packaged article 10 including orthodontic appliance 12 having a base 14 for bonding the appliance 12 to a tooth, an adhesive 16 on the base, and preferably, a release substrate 25 including a surface 27 in contact with the adhesive 16. The adhesive 16 includes a polymerizable component, a fluoride-releasing material, a hydrophilic component, a hardener, an acidic component, and a filler. The release substrate 25 may be selected from a number of materials including, for example, polyolefins, poly(vinyl chloride), polyurethanes, and poly(tetrafluoroethylene). Preferably, the surface 27 of the release substrate 25 comprises a number of pores, and preferably no more than about 50% by weight of the adhesive 16 is within the pores. The article 10 is preferably packaged in a container that provides barriers to the transmission of light and/or water vapor. In some embodiments of the present invention, the article 10 is preferably provided as a kit. In some embodiments, the present invention preferably provides a method of bonding an orthodontic appliance 12 to a tooth.

Some embodiments of the present invention may provide one or more additional features. For example, in some embodiments of the present invention, the adhesive preferably has a static yield stress at 28° C. of at least about 7000 dynes/cm$^2$. In some embodiments of the present invention, the adhesive preferably has a steady state viscosity of about $3\times10^2$ Pa-s to about $7\times10^4$ Pa-s at 28° C.

In some embodiments of the present invention, the adhesive preferably has an initial color prior to exposure to actinic radiation and a final color subsequent to exposure to actinic radiation, with the initial color being different than the final color. In such embodiments, the adhesive preferably includes a photobleachable dye, and the hardener preferably includes a sensitizing compound different from the photobleachable dye.

In some embodiments of the present invention, the adhesive preferably includes a filler including a fumed silica having a surface area of at least about 70 $m^2/g$. Preferably, the filler further includes a base filler.

The adhesives used in the present invention are preferably substantially free of solvent, and substantially free of added water. As used herein, the term "substantially free of added water" means that the composition does not contain water that is intentionally added as a non-complexed or coordinated entity. It is understood that many materials, such as metals or glasses, contain water that is taken up from the atmosphere or is present as a coordination complex in its normal state. Water taken up by hygroscopic materials or present as a hydrate is permissibly present in the compositions described herein. Any water that is present in the composition, regardless of source, should not be present in amounts such that the water will have a deleterious effect on the long term properties of the composition. For example, water should not be present in an amount that would facilitate reaction of an acid-reactive filler with an acidic component so that lumpiness or graininess of the material develops during commercially desired storage times.

Orthodontic adhesives used in the present invention preferably have the ability to uptake water, and therefore are moisture tolerant. It has been surprisingly found that these adhesives retain their strength even when used in moisture contaminated conditions. In orthodontic bracket bonding procedures, for example, it is not necessary to dry the substrate, as long as a coating of moisture tolerant primer is applied to the tooth, prior to bonding the orthodontic appliance. Teeth primed with moisture tolerant primers may become recontaminated as in situations where bonding has been delayed, or where a patient secretes excessive crevicular fluid. Preferably, the adhesives have the ability to absorb moisture from this recontamination situation. Optionally, the primer may also include an etchant composition. Decreased bracket bond failures are expected using orthodontic appliances having these adhesives.

Adhesive

Adhesives used in the present invention include a polymerizable component, a fluoride-releasing material, a hydrophilic component, a hardener, and an acidic component as disclosed, for example, in U.S. Pat. No. 6,126,922 (Rozzi et al.) and International Patent Application Publication No. WO 00/69393 (Brennan et al.).

Hydrophilic Component. Adhesives used in the present invention include a hydrophilic component. Preferably, the hydrophilic component is a hydrophilic monomer, oligomer, or polymer. In a preferred aspect of the present invention, at least some of the hydrophilic component is relatively lower in steady state viscosity than other ingredients of the composition so that it serves as a viscosity lowering function in the overall uncured material. Exemplary hydrophilic components are disclosed, for example, in U.S. Pat. No. 6,126,922 (Rozzi et al.) and International Patent Application Publication No. WO 00/69393 (Brennan et al.).

Preferred hydrophilic components include, for example, 2-hydroxyethyl acrylate, 2-hydroxyethyl methacrylate (HEMA), hydroxypropyl (meth)acrylate, glycerol di(meth) acrylate, poly(ethylene glycol) methacrylate, poly(ethylene glycol) di(meth)acrylate, poly(propylene glycol) (meth) acrylate, tetrahydrofurfuryl (meth)acrylate, glycidyl (meth) acrylate, and combinations thereof. Other preferred hydrophilic monomers include glycerol (meth)acrylate, glycerol di(meth)acrylate, ethylene glycol di(meth)acrylate, poly (ethylene glycol) di(meth)acrylate (where the number of repeating ethylene oxide units varies from 2 to 30, including, for example, tri(ethylene glycol) dimethacrylate (TEGDMA)).

Other examples of hydrophilic components include monomers and polymers such as pyrrolidone, a moiety containing hydroxy groups and polyether groups, a moiety containing a sulfonate group, a moiety containing a sulfinate group, N-oxysuccinimide, N-vinylacetamide, and acrylamide.

Preferably, the adhesive includes at least about 0.05% by weight, more preferably at least about 1% by weight, and most preferably at least about 3% by weight hydrophilic component, based on the total weight of the adhesive. Preferably, the adhesive includes at most about 90% by weight, more preferably at most about 60% by weight, and most preferably at most about 20% by weight hydrophilic component, based on the total weight of the adhesive.

Acidic Component. Adhesives used in the present invention include an acidic component. Preferably, the acidic component is an acidic monomer, oligomer, or polymer. The acidic component includes at least one acidic group. The acidic group is preferably selected from oxyacids or thiooxy acids of C and P. More preferably, the acidic component is a compound that is an acid of C or P. If desired, a precursor to the acid, such as an acid anhydride, e.g., 4-methacryloxyethyl trimellitate anhydride (4-META), or ester can be used in place of the acid itself. For example, the desired acid may be generated in situ. Preferred acids include, for example, carboxylic acids, sulfonic acids, and phenols, with carboxylic acids, alkylsulfonic acids, arylsulfonic acids, and phosphonic acids being more preferred. Exemplary hydrophilic components are disclosed, for example, in U.S. Pat. No. 6,126,922 (Rozzi et al.) and International Patent Application Publication No. WO 00/69393 (Brennan et al.).

Preferred acidic groups are carboxylic acids, sulfonic acids, phosphoric acids, phosphonic acids, and boric acids, the salts of the foregoing acids or precursors of the foregoing acids that are easily converted to these acids in conditions encountered during an orthodontic procedure. Examples of acidic components include, for example, (meth)acryloyl substituted carboxylic acids; phosphoric acid esters of hydroxyethyl (meth)acrylate, hydroxypropyl (meth) acrylate, and glycerol di(meth)acrylate; (meth)acrylates of pentaerythritol (e.g., pentaerythritol di(meth)acrylate); and (meth)acrylates of dipentaerythritol (e.g., dipentaerythritol penta(meth)acrylate), and combinations thereof.

Preferred acidic components include, for example, derivatives of amino acids, and acids such as tartaric acid, citric acid, malic acid that have been functionalized with an ethylenically unsaturated functionality. For example, citric acid may be functionalized by incorporating an acryloyl or methacryloyl functionality. A preferred example of this is CDMA, which is the reaction product of citric acid and isocyanatoethyl methacrylate.

Preferably, the adhesive includes at least about 0.01% by weight, more preferably at least about 0.05% by weight, and most preferably at least about 1% by weight acidic component, based on the total weight of the adhesive. Preferably, the adhesive includes at most about 90% by weight, more preferably at most about 60% by weight, and most preferably at most about 20% by weight acidic component, based on the total weight of the adhesive.

Polymerizable Component. Adhesives used in the present invention include a polymerizable component. Preferably, the polymerizable component is a monomer, oligomer, or polymer that includes a polymerizable group. Exemplary polymerizable components are disclosed, for example, in U.S. Pat. No. 6,126,922 (Rozzi et al.) and International Patent Application Publication No. WO 00/69393 (Brennan et al.). The polymerizable component may also be selected from hydrophilic and acidic components disclosed herein that are polymerizable.

Polymerizable groups may be selected from free radically polymerizable groups, cationically polymerizable groups, or combinations thereof. In a preferred aspect of the present invention, at least some of the polymerizable material is relatively lower in viscosity than other ingredients of the composition so that it serves a viscosity lowering function in the overall uncured material.

Preferred polymerizable groups are free radically polymerizable groups. Preferred free radically polymerizable components are esters of (meth)acrylic acid, including, for example, methyl (meth)acrylate, ethyl (meth)acrylate, propyl (meth)acrylate, isopropyl (meth)acrylate, 2-hydroxyethyl acrylate, 2-hydroxyethyl methacrylate ("HEMA"), hydroxypropyl (meth)acrylate, tetrahydrofurfuryl (meth)acrylate, glycidyl (meth)acrylate, the diglycidyl methacrylate of bisphenol A ("Bis-GMA"), glycerol mono (meth)acrylate, glycerol di(meth)acrylate, ethylene glycol di(meth)acrylate, poly(ethylene glycol) di(meth)acrylate (where the number of repeating ethylene oxide units vary from 2 to 30, including, for example, triethylene glycol dimethacrylate ("TEGDMA")), neopentyl glycol di(meth) acrylate, trimethylolpropane tri(meth)acrylate, mono-, di-, tri-, and tetra-(meth)acrylates of pentaerythritol and dipentaerythritol, 1,3-butanediol di(meth)acrylate, 1,4-butanediol di(meth)acrylate, 1,6-hexanediol di(meth) acrylate, di-2-methacryloyloxethyl hexamethylene dicarbamate, di-2-methacryloyloxyethyl trimethylhexamethylene dicarbamate, di-2-methacryloyloxyethyl dimethylbenzene dicarbamate, methylene-bis-2-methacryloxyethyl-4-cyclohexyl carbamate, di-2-methacryloxyethyl-dimethylcyclohexane dicarbamate, di-1-methyl-2-methacryloxyethyl-trimethyl-hexamethylene dicarbamate, di-1-methyl-2-methacryloxyethyl-dimethylbenzene dicarbamate, di-1-methyl-2-methacryloxyethyl-dimethylcyclohexane dicarbamate, methylene-bis-1-methyl-2-methacryloxyethyl-4-cyclohexyl carbamate, di-1-chloromethyl-2-methacryloxyethyl-hexamethylene dicarbamate, di-1-chloromethyl-2-methacryloxyethyl-trimethylhexamethylene dicarbamate, di-1-chloromethyl-2-methacryloxyethyl-dimethylbenzene dicarbamate, di-1-chloromethyl-2-methacryloxyethyl-dimethylcyclohexane dicarbamate, methylene-bis-2-methacryloxyethyl-4-cyclohexyl carbamate, di-1-methyl-2-methacryloxyethyl-hexamethylene dicarbamate, di-1-methyl-2-methacryloxyethyl-trimethylhexamethylene dicarbamate, di-1-methyl-2-methacryloxyethyl-dimethylbenzene dicarbamate, di-1-methyl-2-methacryloxyethyl-dimethylcyclohexane dicarbamate, methylene-bis-1-methyl-2-methacryloxyethyl-4-cyclohexyl carbamate, di-1-chloromethyl-2-methacryloxyethyl-hexamethylene dicarbamate, di-1-chloromethyl-2-methacryloxyethyl-trimethylhexamethylene dicarbamate, di-1-chloromethyl-2-methacryloxyethyl-dimethylbenzene dicarbamate, di-1-chloromethyl-2-methacryloxyethyl-dimethylcyclohexane dicarbamate, methylene-bis-1-chloromethyl-2-methacryloxyethyl-4-cyclohexyl carbamate, 2,2'-bis(4-methacryloxyphenyl)propane, 2,2'-bis(4-acryloxyphenyl) propane, 2,2'-bis[4-(2-hydroxy-3-methacryloxyphenyl)] propane, 2,2'-bis[4-(2-hydroxy-3acryloxyphenyl)propane, 2,2'-bis(4-methacryloxyethoxyphenyl)propane, 2,2'-bis(4-acryloxyethoxyphenyl)propane, 2,2'-bis(4-methacryloxypropoxyphenyl)propane, 2,2'-bis(4-acryloxypropoxyphenyl)propane, 2,2'-bis(4-methacryloxydiethoxyphenyl)propane, 2,2'-bis(4-acryloxydiethoxyphenyl)propane, 2,2'-bis[3-(4-phenoxy)-2-hydroxypropane-1-methacrylate]propane, 2,2'-bis[3-(4-phenoxy)-2-hydroxypropane-1-acrylate]propane, and combinations thereof.

Preferably, the adhesive includes at least about 0.05% by weight, more preferably at least about 0.1% by weight, and most preferably at least about 0.5% by weight polymerizable component, based on the total weight of the adhesive. Preferably, the adhesive includes at most about 90% by weight, more preferably at most about 60% by weight, and most preferably at most about 20% by weight polymerizable component, based on the total weight of the adhesive.

Fluoride-Releasing Material. Adhesives used in the present invention include a fluoride-releasing material. The fluoride-releasing material may be a filler. The fluoride-releasing material used in the present invention may be naturally occurring or synthetic fluoride minerals, fluoride glass such as fluoroaluminosilicate glass, simple and complex inorganic fluoride salts, simple and complex organic fluoride salts or combinations thereof. Optionally these fluoride sources can be treated with surface treatment agents. The fluoride-releasing material may optionally be a metal complex.

Examples of fluoride-releasing material are fluoroaluminosilicate glasses as described, for example, in U.S. Pat. No. 3,814,717 (Wilson et al.), which may be optionally treated as described, for example, in U.S. Pat. No. 5,332,429 (Mitra et al.). Exemplary fluoride-releasing materials are disclosed, for example, in U.S. Pat. No. 6,126,922 (Rozzi et al.) and International Patent Application Publication No. WO 00/69393 (Brennan et al.).

When the fluoride-releasing material is a glass, preferably the adhesive includes at least about 10% by weight, more preferably at least about 45% by weight, and most preferably at least about 75% by weight fluoride-releasing material, based on the total weight of the adhesive. When the fluoride-releasing material is a glass, preferably the adhesive includes at most about 87% by weight, more preferably at most about 85% by weight, and most preferably at most about 83% by weight fluoride-releasing material, based on the total weight of the adhesive.

Hardener. Adhesives used in the present invention include a hardener. Preferably, the hardener will induce hardening upon exposure to actinic radiation (e.g., the hardener includes a photoinitiator). When the polymerizable component includes free radical polymerizable groups, then the hardener is preferably selected to be a free radical initiator. Exemplary hardeners are disclosed, for example, in U.S. Pat. No. 6,126,922 (Rozzi et al.) and International Patent Application Publication No. WO 00/69393 (Brennan et al.). Preferred free radical photoinitiators include ternary photoinitiator systems as disclosed, for example, in U.S. Pat. No. 5,545,676 (Palazzotto et al.).

Useful visible light induced ternary photoinitiator systems preferably include a sensitizing compound (e.g., camphorquinone), an electron donor (e.g., sodium benzene sulfinate, amines, and amino alcohols), and an iodonium salt (e.g., diphenyliodonium chloride, bromide, iodide, or hexafluorophosphate).

Useful ultraviolet light-induced polymerization initiators preferably include ketones (e.g., benzyl and benzoin), acyloins, and acyloin ethers. Preferred ultraviolet light-induced polymerization initiators include 2,2-dimethoxy-2-phenylacetophenone available under the trade designation IRGACURE 65 and benzoin methyl ether (2-methoxy-2-phenylacetophenone), both available from Ciba Specialty Chemicals, Basel, Switzerland.

The photoinitator is preferably capable of promoting hardening of the polymerizable components on exposure to light of a suitable wavelength and intensity. The photoinitiator is also preferably sufficiently shelf stable and free of undesirable coloration to permit its storage and use under typical orthodontic conditions. Visible light photoinitiators are preferred.

The photoinitiator should be present in an amount sufficient to provide the desired rate of hardening. This amount will be dependent in part on the light source, the thickness of the layer to be exposed to radiant energy, and the extinction coefficient of the photoinitiator. Typically, the photoinitiator components will be present at a total weight of about 0.001% to about 5%, more preferably about 0.01% to about 1%, based on the total weight of the composition.

Optional Photobleachable Dye. In some embodiments of the present invention, the adhesive preferably has an initial color remarkably different than dental structures. Color is preferably imparted to the adhesive through the use of a photobleachable dye. The adhesive preferably includes at least about 0.001% by weight photobleachable dye, and more preferably at least about 0.002% by weight photobleachable dye, based on the total weight of the adhesive. The adhesive preferably includes at most about 1% by weight photobleachable dye, and more preferably at most about 0.1% by weight photobleachable dye, based on the total weight of the adhesive. The amount of photobleachable dye may vary depending on its extinction coefficient, the ability of the human eye to discern the initial color, and the desired color change.

The color formation and bleaching characteristics of the photobleachable dye varies depending on a variety of factors including, for example, acid strength, dielectric constant, polarity, amount of oxygen, and moisture content in the atmosphere. However, the bleaching properties of the dye can be readily determined by irradiating the adhesive and evaluating the change in color. Preferably, at least one photobleachable dye is at least partially soluble in the hardenable resin.

Exemplary classes of photobleachable dyes are disclosed, for example, in U.S. Pat. No. 6,331,080 (Cole et al.) and U.S. patent application Ser. Nos. 09/1489,612, filed Jan. 21, 2000 (now issued as U.S. Pat. No. 6,444,725 (Trom et al.)), and Ser. No. 09/689,019, filed Oct. 12, 2000 (now issued as U.S. Pat. No. 6,528,555 (Nikutowski et al.)). Preferred dyes include, for example, Rose Bengal, Methylene Violet, Methylene Blue, Fluorescein, Eosin Yellow, Eosin Y, Ethyl Eosin, Eosin bluish, Eosin B, Erythosin B, Erxythrosin Yellowish Blend, Toluidine Blue, 4',5'-Dibromofluorescein, and combinations thereof.

The color change in the inventive adhesive is initiated by light. Preferably, the adhesive's color change is initiated using actinic radiation using, for example, a dental curing light which emits visible or near infrared (IR) light for a sufficient amount of time. The mechanism that initiates the color change in the compositions of the invention may be separate from or substantially simultaneous with the hardening mechanism that hardens the resin. For example, an adhesive may harden when polymerization is initiated chemically (e.g., redox initiation) or thermally, and the color change from an initial color to a final color may occur subsequent to the hardening process upon exposure to actinic radiation.

The change in adhesive color from an initial color to a final color is preferably quantified by a Color Test as described below. Using the Color Test, a value of $\Delta E^*$ is determined, which indicates the total color change in a 3-dimensional color space. The human eye can detect a color change of approximately 3 $\Delta E^*$ units in normal lighting conditions. The dental compositions of the present invention are preferably capable of having a color change, $\Delta E^*$, of at least about 20; more preferably, $\Delta E^*$ is at least about 30; most preferably $\Delta E^*$ is at least about 40.

To reduce the degree of color return after the bleaching of the photobleachable dye, the components and component levels used in the adhesive may be selected as desired with guidance from the accompanying specification and examples. For example, the selection of the hardener to include high levels of iodonium salt, the selection of the acidic component to include high levels of CDMA, and the selection of low levels of photobleachable dye may all tend to reduce the degree of color return.

Fillers. Adhesives used in the present invention may optionally include reactive or non-reactive fillers. The filler can have a unimodal or polymodal (e.g., bimodal) particle size distribution. The filler can be an inorganic material. It can also be a crosslinked organic material that is insoluble in the polymerizable resin, and is optionally filled with inorganic filler. The filler is preferably non-toxic and suitable for use in the mouth. The filler can be radiopaque, radiolucent, or non-radiopaque.

Reactive fillers include those that are commonly used with ionomers to form ionomer cements. Examples of suitable reactive fillers include metal oxides such as zinc oxide and magnesium oxide, and ion-leachable glasses including, for example, those described in U.S. Pat. No. 3,655,605 (Smith); U.S. Pat. No. 3,814,717 (Wilson et al.); U.S. Pat. No. 4,143,018 (Crisp et al.); U.S. Pat. No. 4,209,434 (Wilson et al.); U.S. Pat. No. 4,360,605 (Schmitt et al.), and U.S. Pat. No. 4,376,835 (Schmitt et al.). Such reactive fillers may be incorporated to modify the handling characteristics or to affect the setting properties of the ultimate composition.

The reactive filler is preferably a finely divided reactive filler. The filler should be sufficiently finely divided so that it can be conveniently mixed with the other ingredients and used in the mouth. Average particle sizes for the filler are preferably at least about 0.2 micron and more preferably at least about 1 micron. Average particle sizes for the filler are preferably at most about 15 microns and more preferably at most about 10 microns. Average particle sizes may be measured by using, for example, a sedimentation analyzer.

Preferred fillers for use in adhesives used in the present invention include acid-reactive fillers. Suitable acid-reactive fillers include metal oxides, metal salts, and glasses. Preferred metal oxides include barium oxide, calcium oxide, magnesium oxide, and zinc oxide. Preferred metal salts include salts of multivalent cations including, for example, aluminum acetate, aluminum chloride, calcium chloride, magnesium chloride, zinc chloride, aluminum nitrate, barium nitrate, calcium nitrate, magnesium nitrate, strontium nitrate, and calcium fluoroborate. Preferred glasses include borate glasses, phosphate glasses, and fluoroaluminosilicate glasses.

Most preferred of the acid reactive fillers are those that release fluoride. Fluoride releasing glasses, in addition to providing good handling and final composition properties as discussed herein, provide the benefit of long-term release of fluoride in use including, for example, use in the oral cavity. Fluoroaluminosilicate glasses are particularly preferred. Suitable acid reactive fillers are also available from a variety of commercial sources familiar to those skilled in the art. Mixtures of fillers can be used if desired.

If desired acid reactive fillers can be subjected to a surface treatment. Suitable surface treatments include acid washing, treatment with phosphates, treatment with chelating agents such as tartaric acid, and treatment with a silane or silanol coupling agent. Particularly preferred acid reactive fillers are silanol treated fluoroaluminosilicate glass fillers, as described in U.S. Pat. No. 5,332,429 (Mitra et al.).

Non-acid reactive fillers may be selected from one or more of any material suitable for incorporation in compositions used for medical applications, such as fillers currently used in dental restorative compositions and the like. Examples of suitable non-acid reactive inorganic fillers are naturally-occurring or synthetic materials such as quartz, nitrides (e.g., silicon nitride), glasses derived from, for example Ce, Sb, Sn, Zr, Sr, Ba, and Al, colloidal silica, feldspar, borosilicate glass, kaolin, talc, titania, and zinc glass; low Mohs hardness fillers such as those described in U.S. Pat No. 4,695,251 (Randklev); and submicron silica particles (e.g., pyrogenic silicas such as the "Aerosil" Series "OX 50", "130", "150" and "200" silicas sold by Degussa and "Cab-O-Sil M5" and "Cab-O-Sil TS720" silicas sold by Cabot Corp., Boston, Mass.). Examples of suitable non-reactive organic filler particles include filled or unfilled pulverized polycarbonates, polyepoxides, and the like. Preferred non-acid reactive filler particles include quartz, submicron silica, and non-vitreous microparticles of the type described in U.S. Pat. No. 4,503,169 (Randklev). Mixtures of non-acid reactive fillers are also contemplated, as well as combination fillers made from organic and inorganic materials.

Preferably, the surface of the filler particles is treated with a coupling agent in order to enhance the bond between the filler and the polymerizable resin. The use of suitable coupling agents include, for example, gamma-methacryloxypropyltrimethoxysilane, gamma-mercaptopropyltriethoxysilane, gamma-aminopropyltrimethoxysilane, and combinations thereof.

In some embodiments of the present invention, the adhesive preferably includes one or more fumed silica fillers having a surface area of at least about 70 $m^2/g$, more preferably at least about 90 $m^2/g$, and most preferably at least about 100 $m^2/g$. In some embodiments of the present invention, the adhesive preferably includes one or more fumed silica fillers having a surface area of at most about 1000 $m^2/g$, more preferably at most about 500 $m^2/g$, and most preferably at most about 150 $m^2/g$.

Preferably, the adhesive includes at least about 10% by weight, more preferably at least about 45% by weight, and most preferably at least about 75% by weight, based on the total weight of the adhesive, of a base filler. Preferably, the adhesive includes at most about 87% by weight, more preferably at most about 85% by weight, and most preferably at most about 83% by weight, based on the total weight of the adhesive, of a base filler.

Preferably, the adhesive includes at least about 0.1% by weight, more preferably at least about 0.2% by weight, and most preferably at least about 0.5% by weight, based on the total weight of the adhesive, of a fumed silica filler having a surface area of at least about 70 $m^2/g$. Preferably, the adhesive includes at most about 50% by weight, more preferably at most about 15% by weight, and most preferably at most about 3% by weight, based on the total weight of the adhesive, of a fumed silica filler having a surface area of at least about 70 $m^2/g$. It should be recognized that higher levels of base filler will preferably allow lower levels of fumed silica fillers to reach the desired rheological properties, and likewise lower levels of base filler will preferably allow higher levels of fumed silica fillers to reach the desired rheological properties.

Preferably, the adhesive includes a fumed silica filler having an average aggregate length of at least about 0.01 micron, more preferably at least about 0.05 micron, and most preferably at least about 0.1 micron. Preferably, the adhesive includes a fumed silica filler having an average aggregate length of at most about 1 micron, more preferably at most about 0.5 micron, and most preferably at most about 0.4 micron.

If desired, adhesives used in the present invention may optionally include adjuvants. Adjuvants include, for example, cosolvents, pigments, inhibitors, accelerators, viscosity modifiers, surfactants, rheology modifiers, colorants, medicaments, adhesion promoters and other ingredients that will be apparent to those skilled in the art. Optionally, the compositions may contain stabilizers. Suitable adjuvants include, for example, those disclosed in International Patent Application Publication No. WO 00/69393 (Brennan et al.).

Physical Properties. Adhesives used in the present invention preferably have physical properties that are desired for precoated and/or packaged orthodontic appliances and/or adhesives. Desirable properties include, for example, adequate handling properties, no slump that would be observable by a practitioner, suitable operatory light stability, no observable slip when placed on liner or tooth, suitable aesthetic color, color stability under office light conditions (e.g., white light stability), and sufficient tack such that the precoated bracket does not fall off the tooth when placed there prior to curing Adhesives used in the present invention preferably have no substantial flow-out. Flow-out value is a measure of the tendency of an adhesive to flow on a liner, and is measured by a test method as described in the Examples. In brief, flow-out is measured by coating an adhesive on an orthodontic bracket, placing the adhesive on the coated bracket in contact with a release substrate, and holding for a specified time at a specified temperature (e.g., one week at 40° C.). The flow-out is measured as flow out of the adhesive from the edge of the bracket in millimeters.

Adhesives used in the present invention preferably have a steady state viscosity at 28° C. of at least about $3 \times 10^2$ Pa-s, more preferably at least about $5 \times 10^3$ Pa-s, and most preferably at least about $1 \times 10^4$ Pa-s. Adhesives used in the present invention preferably have a steady state viscosity at 28° C. of at most about $7 \times 10^4$ Pa-s, more preferably at most about $2.5 \times 10^4$ Pa-s, and most preferably at most about $2 \times 10^4$ Pa-s.

Adhesives used in the present invention preferably have a static yield stress at 28° C. of at least about 7,000 dynes/$cm^2$, more preferably at least about 8,000 dynes/$cm^2$, and most preferably at least about 9,000 dynes/$cm^2$. Adhesives used in the present invention preferably have a static yield stress at 28° C. of at most about 100,000 dynes/$cm^2$, more preferably at most about 60,000 dynes/$cm^2$, and most preferably at most about 25,000 dynes/$cm^2$.

The adhesives used in the present invention may be applied to the base of the orthodontic appliance by methods known in the art. Suitable methods include, for example, application with a syringe or other suitable dispensing devices as disclosed, for example, in U.S. Pat. No. 5,552,177 (Jacobs et al.).

Release Substrate

Articles of the present invention preferably include a release substrate in contact with the adhesive. Preferably, a surface of the release substrate includes a number or pores, and no more than about 50% by weight of the adhesive is in the pores. Preferably, the release substrate includes a foam. Suitable release substrates are disclosed, for example in U.S. Pat. No. 6,183,249 (Brennan et al.). Preferably, the release substrate is a crosslinked polyethylene foam available under the trade designation MINICEL (e.g., MINICEL M200) from Voltek (Lawrence, Mass.). Preferably, the release substrate provides for easy release of the appliance and reduced slip and flow-out.

The release substrates used in the present invention may be applied to the adhesive on the base of the orthodontic appliance by methods known in the art. Suitable methods include, for example, placing the release substrate on the bottom of a container well and then lightly inserting the bracket in the well such that the adhesive is in contact with the release substrate. A robotic arm may be used, for example, as described in U.S. Pat. No. 5,552,177 (Jacobs et al.).

The articles of the present invention are prefexably packaged in a container for storage and distribution. Suitable containers include, for example, those disclosed in U.S. Pat. No. 4,978,007 (Jacobs et al.), U.S. Pat. No. 5,172,809 (Jacobs et al.), U.S. Pat. No. 5,328,363 (Chescr et al.), U.S. Pat. No. 5,354,199 (Jacobs et al.), U.S. Pat. No5,538,129 (Chester et al.), U.S. Pat. 5,575,645 (Jacobs et al.), and in coassigned U.S. patent application Ser. No. 10/126,804 (published as US 2003-0196914 A1), filed on Apr. 18, 2001, and entitled "CONTAINERS FOR PHOTOCURABLE MATERIALS". Optionally, the container may include a release substrate. The release substrate may optionally be part of the container, but preferably the release substrate is a release liner.

The articles disclosed in the present invention may be included in kits. In addition to having one or more articles of the present invention, kits preferably include additional components including, for example, instructions for using the orthodontic appliance, etching compositions, swabs or brush tips for etching compositions, appliance placement guides or jigs, extra quantities of adhesive, primer, sealant, and mix pads.

Methods of using the presently disclosed article include separating the orthodontic appliance from the release substrate, wherein the adhesive preferably remains on the base of the orthodontic appliance. The orthodontic appliance is then applied to the tooth surface and positioned properly by the practitioner so that the adhesive is in intimate contact with the surface of the tooth. When properly positioned, the adhesive is hardened by exposure to actinic radiation. Optionally, the surface of the tooth may be etched and dried before adhering the adhesive-coated bracket to the tooth. If desired, a coating of primer may be applied to the tooth prior to adhering the adhesive-coated bracket to the tooth. When a primer is used, the drying step may or may not be required, depending upon the type of primer applied. Optionally, the etchant may include a primer.

Preferably, after the adhesive is applied to a moistened tooth surface and hardened, the appliance is bonded to the tooth with a bond strength of at least about 7 MPa, more preferably at least about 9 MPa, and most preferably at least about 11 MPa. Preferably, after the adhesive is hardened, the appliance is bonded to the tooth with a bond strength of at most about 25 MPa.

The present invention is illustrated by the following examples. It is to be understood that the particular examples, materials, amounts, and procedures are to be interpreted broadly in accordance with the scope and spirit of the invention as set forth herein.

EXAMPLES

The following examples are given to illustrate, but not limit, the scope of this invention. Unless otherwise indicated, all parts and percentages are by weight and all molecular weights are weight average molecular weight.

| ABBREVIATIONS, DESCRIPTIONS, AND SOURCES OF MATERIALS | |
|---|---|
| BisGMA | 2,2-Bis[4-(2-hydroxy-3-methacryloyloxypropoxy)phenyl]propane (CAS No. 1565-94-2) |
| PEGDMA | Polyethylene glycol-400 dimethacrylate (Rhom Tech, Inc., Linden, NJ) |
| GDMA | Glycerol dimethacrylate (Rhom Tech, Inc.) |
| CDMA | Reaction product of citric acid and IEM as described herein |
| CDMA-PEGDMA | Two parts by weight CDMA dissolved in one part by weight PEGDMA |
| DUDMA | Diurethane dimethacrylate (Huls of America, Feasterville, PA) |
| pNVP | Poly(N-vinylpyrrolidone); PLASTONE K-29/31 (International Specialty Products, Wayne, NJ) |
| IEM | 2-Isocyanatoethyl methacrylate (Sigma-Aldrich Fine Chemicals, St. Louis, MO) |
| CPQ | Camphorquinone (Sigma-Aldrich) |
| BHT | 2,6-Di-tert-butyl-4-methylphenol (Sigma-Aldrich) |
| EDMAB | Ethyl 4-(N,N-dimethylamino)benzoate (Sigma-Aldrich) |
| DPIHFP | Diphenyl Iodonium Hexafluorophosphate (Johnson Matthey, Alpha Aesar Division, Ward Hill, NJ) |
| DBTDL | Dibutyltin Dilaurate (Sigma-Aldrich) |
| Tinuvin-P | UV Inhibitor (Ciba Specialty Chemicals Corp., Terrytown, NJ) |
| TPS | Triphenylantimony (Elf Atochem North America, Philadelphia, PA) |
| EYB | Erythrosin Yellowish Blend Dye (Blend of 90 parts by weight Erythrosin and 10 parts by weight Eosin Y) (Sigma-Aldrich) |
| TS720 | Fumed (pyrogenic) silica; surface-treated with dimethyl silicone fluid; surface area about 105 to about 130 $m^2$/gram (CAB-O-SIL TS720, Cabot Corp., Boston, MA) |
| CAB-O-SIL M5 | Fumed (pyrogenic) silica; surface area about 175 to about 235 $m^2$/gram (CAB-O-SIL MS, Cabot Corp.) |
| R-972 | Fumed (pyrogenic) silica; surface-treated with dimethyldichlorosilane; surface area about 90 to about 130 $m^2$/gram (AEROSIL R-972, Degussa Corp., Akron, OH) |
| OX-50 | Fumed (pyrogenic) silica; surface area about 35 to about 65 $m^2$/gram (AEROSIL OX-50, Degussa Corp.) |
| S/T OX-50 | Silane-treated OX-50; prepared as described in Preparatory Example 2 in International Patent Application Publication No. WO 00/69393 (Brennan et al.) |
| S/T FAS | Silane-treated fluoroaluminosilicate glass (FAS); prepared as described in Preparatory Example 1 in International Patent Application Publication No. WO 00/69393 (Brennan et al.) |

Test Methods

Static Yield Stress and Steady State Viscosity

Measurement of the yield stress and viscosity of adhesive test samples was performed with a Rheometrics ARES controlled strain rheometer (Advanced Rheometric Expansion System, Rheometric Scientific, Inc., Piscataway, N.J.). The rheometer was fitted with parallel plates of 25-mm diameter. An environmental chamber held the temperature in the immediate vicinity of the fixtures and sample at 28° C. Adhesive samples were prepared at least 24 hours prior to measurement by pressing the samples between two sheets of SCOTCHPAK 1022 release liner (3M Company) to a thickness of approximately 2.5 mm and a diameter of at least 25 mm.

These samples were placed on the lower plate of the rheometer using a spatula to facilitate removal from the release liner. The upper plate was lowered until contact with the adhesive sample was made. The environmental chamber was then closed and the rheometer set to automatically close the plates to a gap of 2.2 mm. The chamber was then opened and the excess adhesive trimmed from the edges of the plates using a razor blade. The chamber was then closed again and the rheometer set to automatically close the plates to a gap of 2.0 mm.

After closing the chamber the rheometer was then programmed to wait for 10 minutes for the temperature to stabilize at 28° C. before beginning the measurement. The rheometer was then programmed to shear the adhesive sample at a shear rate of 0.01 second$^{-1}$ for 30 seconds followed by shearing at 0.1 second$^{-1}$ for 4.5 minutes. During each of these periods the rheometer collected stress measurements.

The yield stress of an adhesive sample was defined as the point at which the stress vs. time curve deviated from an initially linear trajectory. Practically, this was determined by constructing a tangent to the stress vs. time curve. The tangent was then shifted by 0.06 seconds to the right and the intercept with the stress vs. time curve determined. This intercept, being very close to the point of deviation from linearity, was defined as the static yield stress (or as the transition from elastic deformation to viscoelastic flow) and reported as dynes/cm$^2$ for the adhesive sample. Reported values were from single measurements of the samples.

The adhesive samples were thixotropic, meaning that the viscosity under constant shear rate changes with time. Therefore, the viscosity of an adhesive sample was defined as the viscosity measured after a given time under shear. This time was chosen such that any yield stresses would have been overcome. A period of 3.5 minutes at 28° C. under a shear rate of 0.1 second$^{-1}$) was chosen since by that time all of the adhesive samples measured were well beyond yielding. The results were reported as steady state viscosity values (from single measurements) in units of Pa-s (Pascal-seconds).

Water Uptake

Water uptake was measured by forming each adhesive sample into a cylinder 4-mm in diameter and 4-mm thick using a Teflon mold that was open on both ends. To keep the uncured adhesive in place, the opposite end from that being charged (i.e., the bottom end) was set against polyethylene terephthalate ("PET") film that was placed on white paper. The top end was then covered with PET film and light-cured for 30 seconds using an ORTHOLUX XT Visible Light Curing Unit (3M Unitek). Intimate contact between the PET covered sample and the light guide was ensured. The PET films were then removed and the cylinder of cured material was removed from the mold. Within one hour, each cured cylinder was weighed and placed in a glass vial to which was added 8 ml of deionized water. Each sample was maintained at 40° C. for periods of two and ten days.

At the specified times, a cylinder sample was removed from the vial, the superficial water was removed using a facial tissue or cotton, and the sample was immediately weighed. The weight recorded and water uptake for 2 samples of each composition was measured and the average reported in % increased water weight (defined as Water Uptake Value).

Adhesive/Bracket Flow-Out

The Adhesive/Bracket Flow-Out Test Method was used to determine the tendency of an adhesive to flow on a liner beneath an orthodontic bracket, a phenomenon called "flow-out". If an adhesive exhibits flow-out on a specific liner in this test, then the adhesive would be expected to flow-out within a blister package containing the adhesive precoated on a bracket and covered with the same liner. Flow-out can produce stringing of the adhesive away from the bracket base as the adhesive precoated bracket is removed from the liner. This result can cause difficulties for a practitioner who must then make adjustments to the shape of the adhesive pad (or pillow) prior to placement of the adhesive precoated bracket on the tooth. In the worst case, flow-out prevents full release of the adhesive from the liner, which may even cause separation of the adhesive from the precoated bracket.

Mini Twin V-slot brackets (3M Unitek, Ref #017-333 or 017-334) were coated by application from a syringe with about 8 mg of adhesive placed on a SCOTCHPAK 1022 release liner (3M Company) with the adhesive in contact with the liner, and held for one week in a 40° C. oven. (Time and temperature of the test was varied depending upon the test sample.) The adhesive precoated brackets were placed on liners that were held to cardboard via double stick tape in order to keep the brackets in a horizontal position in the oven. Special precaution was taken to ensure that no adhesive was visible beyond the bracket base at the start of the test. After 1 week (or other pre-determined time), adhesive flow-out beyond the bracket base was measured using RAM Optical Instrumentation (Omis Mini with AutoMap XYZ measurement software, RAM Optical Instrumentation, Huntington Beach, Calif.). Flow-out values were measured only for the worst edge (i.e., greatest flow-out) of each bracket base (rather than taking an average of flow-out on each of the 4 edges of the bracket base) and each reported value was an average of at least 3 adhesive precoated bracket samples. It is noted that about 0.01 inch (about 0.25 mm) of flow-out is barely detectable to the naked eye; however, 0.02 inch (about 0.51 mm) is readily detectable to the naked eye and can lead to problems of adhesive separation from the release liner.

Adhesive/Bracket Vertical Slip

The Adhesive/Bracket Vertical Slip Test Method was developed to determine if adhesive precoated brackets using specific adhesive compositions would slip on specific release liners in blister packages. If an adhesive exhibits slippage on a specific liner in this test, then the adhesive would be expected to slip (e.g., during transit to the customer) within a blister package containing the adhesive precoated on a bracket and covered with the same liner. In the worst case, the adhesive precoated brackets may slip entirely off the liner, destroying the product functionality. Or, the adhesive precoated bracket may rotate in the package, which would result in improper orientation for placement of the bracket on the tooth by the practitioner.

3M Unitek Mini Twin V-slot, (Ref. 017-333 or 017-334) or buccal tubes (Ref. 067-8033) or Victory Series (Ref. 017-401) brackets were coated by application from a syringe with about 8 mg of adhesive (with the exception of buccal tubes which were coated with about 16 mg of adhesive). The adhesive precoated brackets were placed on MINICEL M200 foam liner (Voltek Corp, Division of Sekisui America, Lawrence, Mass.). Each liner containing the adhesive precoated bracket was held to a piece of cardboard via double stick tape. Special precaution was taken to ensure that no adhesive was visible beyond the bracket base at the start of the test. A "starting line" was drawn near the top edge of the bracket to ensure measurement of the exact distance of slippage. The cardboard containing the brackets was held vertically in an oven (set at a predetermined temperature, typically 40° C. or 50° C.) for predetermined period of time (typically 3 to 14 days). Slippage of the adhesive coated bracket on the liner was measured as flow-out beyond the top edge of the bracket base and was measured using RAM Optical Instrumentation as described in the preceding test method. The slippage values reported (in mm) were an average of at least 3 adhesive precoated bracket samples per test.

Fluoride Release

Fluoride release was measured by first forming sample compositions into disks 20-mm in diameter and 1-mm thick. Both sides of each disk were covered with polyethylene terephthalate film and light-cured for 60 seconds on each side using two oppositely disposed VISILUX 2 Visible Light Curing Units (3M Company) with about a 1-cm distance between the output end of the light guide and the sample disk. The film was then removed from both sides of the disks and the samples allowed to cure for 1 hour at 37° C./95% relative humidity ("RH"). Each disk was weighed and placed in a glass jar to which was added 25 ml of deionized water. The sample solutions were maintained at 37° C. for specified time periods at which times the incremental fluoride release was measured as follows.

A fluoride-selective electrode, Orion Model 96-09-00 (Orion Research Inc., Cambridge, Mass.) was used to quantify the amount of fluoride ion released from the sample disks in water. The electrode was calibrated using Fluoride Activity Standards #940907 and #040908, at 100 parts per million ("ppm") and at 10 ppm, respectively, fluoride standard fluid (both from Orion Research Inc.).

For measurement of fluoride ions released into water, 10 ml of the sample solution was transferred to a 60-ml beaker containing 10 ml of TISAB solution (total ionic strength adjustment buffer; Orion Research Inc., Cambridge, Mass.). The contents were mixed for 10 seconds. The calibrated fluoride-selective electrode was placed in the solution and the fluoride concentration in ppm was recorded and converted to micrograms of fluoride per gram of the cured disk. The residual liquid was then removed from the sample jar and replaced with a fresh 25-ml quantity of deionized water. The sample jar was transferred to a 37° C. oven for a specified time interval after which the sample jar was removed from the oven and the fluoride released during that time interval was measured as described herein. Fluoride release values were reported as a function of storage time in the water and each reported value represented the average of 3 sample disks.

Bond Strength for Moisture Tolerance

Bond strength was tested by adhering metal orthodontic brackets with mesh bases to bovine teeth using an adhesive sample. The adhesive sample was applied by syringe to VICTORY SERIES REF 017-401 (or equivalent) upper central brackets (3M Unitek). The bovine teeth were first cleaned with a pumice aqueous slurry and rinsed. The teeth were then etched with 37% phosphoric acid etching solution, rinsed with water and dried with moisture-free and oil-free air. The teeth were then treated with TRANSBOND MIP moisture insensitive primer (3M Unitek) according to manufacture's directions. The metal brackets with applied adhesive were seated onto the teeth and pressed firmly to extrude any excess adhesive. The excess was cleaned away. The adhesive was then cured with 10-second exposures on both the mesial and distal sides of the brackets using an ORTHOLUX XT Curing Unit. The samples of teeth and bonded brackets were stored overnight in 37° C. water. Bond strength testing was performed by engaging a 0.50-mm round stainless steel wire loop under the occlusal tie wings. Using an Instron universal load frame, a load was applied in a shear/peel mode until debonding of the bracket from the tooth occurred. The wire attached to the Instron was pulled at a rate of 5 mm/minute. The maximum force (in units of pounds) was recorded as bond strength per bracket and the reported value was an average of 10 measurements using 10 different adhesive-coated brackets. This average was then converted to units of MPa by dividing by the bonding base area (10.9 mm$^2$) and multiplying by 4.4.

In a variation of this test method, moisture (in the form of distilled water by a spray bottle or saliva by a cotton swab) was applied to the bovine teeth after treatment with TRANSBOND MIP primer and before bonding of the adhesive-coated brackets to the teeth. Results were reported as averages of 5 measurements using 5 different adhesive-coated brackets.

Color Test

Quantification of initial and bleached color of adhesive samples was performed with a StellarNet Portable Spectrometer Model EPP2000C equipped with a 400-micron fiber reflectance probe and SpectraWiz CIELAB colorimeter software (StellarNet, Inc., Oldsmar, Fla.).

To prepare samples for color measurement, an adhesive sample was extruded onto a polyester release liner, a metal ring was placed around the adhesive, and a second release liner was placed on top of the adhesive. The resulting construction was then pressed between two Plexiglas plates with the metal ring controlling the adhesive thickness to 0.51 mm. With the light source of the spectrometer switched off, the adhesive sample between the two release liners was placed on top of a white reflectance standard (Part No. RS50, 50-mm diameter, Halon type >97% reflectance, 300-1500 nm, StellarNet, Inc.). The fiber optic probe of the spectrometer was positioned 6.3 mm above the sample at a 45° angle. Color measurements were taken through the top release liner at an exposure time of 1000 milliseconds and with the center of the adhesive under the beam. The software captured the reflectance spectrum and converted the input to L*, a* and b* values. The a* value was indicative of the redness of the sample with higher numbers indicative of greater redness.

Cured adhesive samples were prepared in the same manner described herein, except that the adhesive pressed between the two polyester release liners was cured for 3 minutes in a TRIAD 2000 light curing oven (Dentsply International, Inc., York, Pa.). The cured adhesive sample with the polyester liners intact was placed directly onto the white reflectance standard. The light source of the spectrometer was switched on and L*, a* and b* values were measured as described herein with each reported value representing the average of 3 measurements.

White Light Stability

Adhesive samples were prepared as described herein for the Color Test Method. Five samples were made by pressing the adhesive between polyester release liners to a disk shape having a thickness of 0.51 mm. One adhesive disk was measured immediately and used as the zero point. The remaining four disks were placed onto a sheet of white paper and placed at desk height directly below a fluorescent light fixture at standard ceiling height. The distance between the fluorescent light and the adhesive samples was approximately 2.0 meters. Adhesive samples were removed from fluorescent light exposure after 2, 5, 10 and 20 minutes exposure and moved to a dark room. Colors of the samples were then measured as described herein for the Color Test Method. Results for a* could then be reported as a function of exposure to fluorescent lighting with each reported value representing a single measurement.

Starting Material Preparations

CDMA

CDMA is defined as the reaction product of citric acid and IEM as prepared according to the following procedure. Citric acid (1870 g; 9.733 moles citrate, 29.2 moles carboxylate) was dissolved in tetrahydrofuran (5.9 liters) in a reaction vessel fitted with a mechanical stirrer, condenser, addition funnel, and air inlet tube. To the resultant homogenous solution were added BHT (4.69 g), TPS (4.68 g), and DBTDL (4.68 g). Dry air was introduced into the reaction mixture through the inlet tube, and IEM (3019 g; 19.46 moles) was added dropwise through the addition funnel at a rate to maintain the reaction temperature at about 40° C. The reaction was followed by infrared spectroscopy and gas chromatography. After all the IEM had been added and the IR spectrum no longer showed the presence of isocyanate groups, the solvent was removed under vacuum from the reaction mixture to afford a viscous liquid. Nuclear magnetic resonance spectroscopy confirmed the presence of added methacrylate functionalities and the retention of carboxy groups. For use in subsequent formulation studies, the viscous liquid (CDMA) was dissolved in PEGDMA in a weight ratio of 1 part PEGDMA to 2 parts CDMA. The resulting solution was designated CDMA-PEGDMA.

Filler A (Silane-treated Quartz Filler)

Filler A was a silane-treated quartz filler prepared according to the following procedure. A 58.3-g portion of deionized water was weighed into a 1000-ml beaker. The water was preheated to about 29° to 33° C. While stirring with a magnetic stirrer, 105 g of quartz filler (Coleman Quartz, Jessieville, Ark.) was added to the water followed by the slow addition of 1.7 g of AEROSIL R-972 fumed silica. The pH of the resulting slurry was adjusted to between about 2.5 and 3.0 with 1% trifluoroacetic acid (Sigma-Aldrich). Mixing was continued for five minutes, followed by the addition of 3 g of 3-methacryloxypropyltrimethoxysilane (United Chemical Technologies, Inc., Bristol, Pa.). The resulting slurry was stirred for two hours and then poured evenly into a tray lined with polyester sheeting. The filled tray was placed in a convection drying oven for 12 hours at about 60° C. to yield a dry cake. The dried cake was crushed using a mortar and pestle, dried for 8 hours at about 60° C., and the crushed filler was screened though a 74 micrometer nylon screen to afford the powder filler designated as Filler A.

Filler B (Silane-treated FAS Filler)

Filler B was a silane-treated fluoroaluminosilicate glass (FAS) filler prepared according to the following procedure. A 6,420-g portion of deionized water was weighed into a 23-liter polyethylene pail. The water was stirred with a Premier electric mixer (Premier Mill, Reading, Pa.) so as to create a vortex of about 2.5 mm in depth about the mixer shaft and adjusted to a pH of about 3.0 with the addition of about 90 g of glacial acetic acid. To the resulting acidic solution was added 521 g of 3-methacryloxypropyltrimethoxysilane (United Chemical Technologies, Inc.). The solution was stirred for 1 hour and then charged with 5990 g of finely powdered, FAS glass (Schott Glas, Landshut, Germany). The resulting slurry was stirred for 30 minutes and then poured evenly into a tray lined with polyester sheeting. The filled tray was placed in a convection drying oven for 16 hours at about 80° C., followed by an additional 2 hours at 100° C. to yield a dry cake. The dried cake was crushed using a mortar and pestle and the crushed filler was screened though a 74 micrometer nylon screen to afford the powder filler designated as Filler B.

Examples 1–10 and Comparative Examples 1–3

Compositions (e.g., adhesives) of the present invention (Examples 1–10) and Comparative Examples 1–3 were prepared according to the following procedures.

A resin precursor was first prepared by charging the resin components shown in Tables 1A and 1B into a vessel. The resulting mixture was heated to 45° C. and stirred using an electric stirring motor (Fisher Scientific, model #47) fitted with a glass stirring rod and 2.54-cm Teflon stirring blade. Mixing speed was adjusted so as to create a vortex of about 6 mm. The mixing vessel was shielded from light and the mixing continued for 4 hours to dissolve all solid components. Each resin precursor was then combined with the filler components shown in Tables 1A and 1B mixed until a homogeneous, paste like composition was achieved.

For Examples 2, 3 and 5–9 mixing of the resin precursor with the filler components was accomplished using a planetary mixer (Charles Ross and Co, Hauppauge, N.Y.) of sufficient size (0.95 to 3.785 liters) to accommodate the amounts of materials charged. Example 10 and Comparative Example 3 were mixed using a 15-liter planetary mixer (Premier Mill, Reading Pa.). Generally, the resin precursor was charged first to the mixing vessel followed by the filler components. The entire filler amount was charged at once and then mixed until the desired, paste-like consistency was achieved; or, alternatively, a portion of the total filler was withheld from the initial mixture and incorporated in subsequent mix cycles. Typically, a total of 1 to 4 additional filler mix cycles was utilized. Homogeneity of the paste depended on several factors, e.g., mix time, planetary mix speed, resin viscosity, and total amount of filler added. For the examples mixed in a planetary mixer, all were done at 45° C. and at a mixing speed of 10 to 12 rpm.

For Examples 1 and 4 and Comparative Examples 1 and 2, mixing of the resin precursor with the filler components was accomplished using a Hauschild Speed Mixer {T} System (Flack Tec Inc, Landrum, S.C.). This type of mixer differed from the more traditional mixers (e.g., planetary mixers) in that the resin precursor and filler components were charged to a vessel and mixing was accomplished through centrifugal forces created by rapidly spinning the vessel and its contents. For the examples mixed by this method, the entire amounts of resin and filler components were charged into a 40-ml plastic mixing vessel and mixed at room temperature for 1 minute at 3,000 rpm to afford a homogeneous composition.

All of the compositions of Examples 1–10 and Comparative Examples 1 (CE-1) and 2 (CE-2) contained more than one filler component. For Examples 1, 6–8, CE-1 and CE-2 filler components could be added independently in the amounts shown in Tables 1A and 1B. Alternatively, the filler components could be combined to form a filler precursor prior to charging to the resin precursor in the mixing vessel. Such filler precursors were prepared and used to make the compositions of Examples 2–5 and 9–10. Such admixing was accomplished by mixing small amounts by hand in a convenient sized beaker or, alternatively, for larger amounts of materials, blending was accomplished using, a Patterson Kelley Twin Shell Blender (Harsco Corp., Camp Hill, Pa.) as was done for Example 10.

For each Example and Comparative Example listed in Tables 1A and 1B, resin and filler components are listed in percent by weight based on the total weight of the composition.

TABLE 1A

Compositions of Examples 1–8

| Component | Ex. 1 | Ex. 2 | Ex. 3 | Ex. 4 | Ex. 5 | Ex. 6 | Ex. 7 | Ex. 8 |
|---|---|---|---|---|---|---|---|---|
| Resin Components (Percent by weight based on total weight of the composition) | | | | | | | | |
| CDMA-PEGDMA | 6.59 | 6.52 | 10.75 | 11.13 | 12.92 | 13.84 | 6.62 | 6.65 |
| PEGDMA | 6.59 | 6.52 | 5.61 | 5.81 | 6.75 | 0.727 | 6.62 | 6.65 |
| BisGMA | 7.31 | 7.15 | 1.02 | 1.05 | 1.22 | 8.075 | 7.26 | 7.29 |
| BHT | 0.021 | 0.104 | 0.089 | 0.093 | 0.107 | 0.018 | 0.027 | 0.027 |
| CPQ | 0.065 | 0.042 | 0.027 | 0.037 | 0.043 | 0.055 | 0.065 | 0.065 |
| DPIHFP | 0.158 | 0.156 | 0.134 | 0.139 | 0.161 | 0.046 | 0.158 | 0.042 |
| EDMAB | 0.263 | 0.259 | 0.223 | 0.231 | 0.268 | 0.225 | 0.263 | 0.264 |
| EYB | 0 | 0.004 | 0.004 | 0.004 | 0.004 | 0.012 | 0.000 | 0.011 |
| Filler Components (Percent by weight based on total weight of the composition) | | | | | | | | |
| Filler A | 38.88 | 39.00 | 40.42 | 40.10 | 38.63 | 37.88 | 39.01 | 39.01 |
| Filler B | 38.88 | 39.00 | 40.42 | 40.10 | 38.63 | 37.88 | 39.01 | 39.01 |
| TS720 | 1.25 | 1.25 | 1.31 | 1.30 | 1.26 | 1.25 | 0.988 | 0.988 |

TABLE 1B

Compositions of Examples 9–10 and Comparative Examples (CE) 1–3

| Component | Ex. 9 | Ex. 10 | CE-1 | CE-2 | CE-3 |
|---|---|---|---|---|---|
| Resin Components (Percent by weight based on total weight of the composition) | | | | | |
| CDMA-PEGDMA | 12.03 | 12.36 | 11.85 | 14.97 | 0 |
| PEGDMA | 6.28 | 6.45 | 3.95 | 0 | 0 |
| BisGMA | 1.14 | 1.17 | 3.33 | 3.33 | 0 |
| DUDMA | 0 | 0 | 0.83 | 1.66 | 0 |
| pNVP | 0 | 0 | 0.67 | 0.67 | 0.821 |
| CDMA | 0 | 0 | 0 | 0 | 6.40 |
| GDMA | 0 | 0 | 0 | 0 | 11.23 |
| BHT | 0.101 | 0.104 | 0.02 | 0.02 | 0.017 |
| CPQ | 0.04 | 0.042 | 0.05 | 0.05 | 0.049 |
| DPIHFP | 0.152 | 0.156 | 0.10 | 0.10 | 0.217 |
| EDMAB | 0.455 | 0.467 | 0.20 | .20 | 0.182 |
| Tinuvin-P | 0 | 0 | 0 | 0 | 0.091 |
| EYB | 0.006 | 0.005 | 0 | 0 | 0 |
| Filler Components (Percent by weight based on total weight of the composition) | | | | | |
| Filler A | 39.26 | 38.99 | 0 | 0 | 0 |
| Filler B | 39.26 | 38.99 | 0 | 0 | 0 |
| S/T FAS | 0 | 0 | 75.05 | 71.10 | 79.06 |
| OX-50 | 0 | 0 | 3.95 | 7.90 | 0 |
| S/T OX-50 | 0 | 0 | 0 | 0 | 1.94 |
| TS720 | 1.28 | 1.27 | 0 | 0 | 0 |

Examples 11–20

Examples 11–15 were prepared by blending small quantities of various fumed silica materials of high surface area into the composition designated Comparative Example 1. Examples 16–20 were prepared by blending small quantities of various fumed silica materials of high surface area into the composition designated Comparative Example 2. The specific fumed silica materials used and the quantities of fumed silica added are shown in Table 2. In each case, the addition of high surface area fumed silica caused a significant change in the physical characteristics of the compositions and the degree of this change was dependent on the amount and type of fumed silica added. With the addition of small amounts of fumed silica of high surface area, pastes were transformed from highly flowing pastes in the case of the starting compositions (Comparative Examples 1–2) to non-flowing, non-slumping pastes in the case of the resulting compositions (Examples 11–20). It was observed that CAB-O-SIL M5 modifications resulted in the most dramatic increases in viscosity (Examples 11–13 and 16–18) and ability to modify the flow behavior of the starting compositions, particularly when added at levels of 0.5% by weight and higher. The addition of 0.5% by weight CAB-O-SIL TS720 or Aerosil R972 to the starting compositions (Comparative Examples 1–2) resulted in only minor changes in viscosity, but significantly transformed the pastes of the starting compositions into non-flowing and non-slumping pastes (Examples 14–15 and 19–20).

TABLE 2

Examples 11–20
(Comparative Examples 1–2 with Added Fumed Silicas)

| | | Added Fumed Silica | |
|---|---|---|---|
| Example | Starting Composition | Fumed Silica | Amount Added (Wt. %) |
| 11 | Comparative Ex. 1 | CAB-O-SIL M5 | 1.00 |
| 12 | Comparative Ex. 1 | CAB-O-SIL M5 | 0.50 |
| 13 | Comparative Ex. 1 | CAB-O-SIL M5 | 0.25 |
| 14 | Comparative Ex. 1 | AEROSIL R972 | 0.50 |
| 15 | Comparative Ex. 1 | CAB-O-SIL TS720 | 0.50 |
| 16 | Comparative Ex. 2 | CAB-O-SIL M5 | 1.00 |
| 17 | Comparative Ex. 2 | CAB-O-SIL M5 | 0.50 |
| 18 | Comparative Ex. 2 | CAB-O-SIL M5 | 0.25 |
| 19 | Comparative Ex. 2 | AEROSIL R972 | 0.50 |
| 20 | Comparative Ex. 2 | CAB-O-SIL TS720 | 0.50 |

Evaluations and Results

Static Yield Stress and Steady State Viscosity: The Static Yield Stress and Steady State Viscosity were measured for Examples 11–20, Comparative Examples 1–3, and the commercial product TRANSBOND XT orthodontic adhesive (3M Unitek) according to the Test Method described herein. Results are reported in Table 3 and show that the addition of low levels of various high surface area fumed silica materials to adhesive compositions CE-1 and CE-2, which contained the fumed silica OX-50 at levels of 3.95% and 7.90%, respectively, afford compositions (Examples 11–20) with increased yield stress (with the exception of Example 13 which contained 0.25% fumed silica) and viscosity. In the case of certain Examples (e.g., Examples 11–12, 14–17, 19–20), the addition of OX-50 afforded rheological properties highly desirable for use as adhesives in packaged adhesive-coated orthodontic appliances. The commercial product TRANSBOND XT also possesses desirable rheological properties for such applications, however, the product is of low hydrophilicity and lacks fluoride-releasing capability (e.g., does not contain a fluoride-releasing component).

TABLE 3

Static Yield Stress and Steady State Viscosity Results

| Example | Fumed Silica Content (Weight %) | Static Yield Stress (Dyne/Cm$^2$ × 10$^3$) | Steady State Viscosity (Pa-seconds × 10$^4$) |
| --- | --- | --- | --- |
| CE-1 | OX-50 (3.95) | 6.2 | 1.1 |
| 11 | CE-1 + CAB-O-SIL M5 (1.0) | 36 | 4.9 |
| 12 | CE-1 + CAB-O-SIL M5 (0.5) | 14 | 2.6 |
| 13 | CE-1 + CAB-O-SIL M5 (0.25) | 5.1 | 1.2 |
| 14 | CE-1 + AEROSIL R972 (0.5) | 7.3 | 1.6 |
| 15 | CE-1 + CAB-O-SIL TS-720 (0.5) | 10 | 2.2 |
| CE-2 | OX-50 (7.90) | 6.9 | 1.1 |
| 16 | CE-2 + CAB-O-SIL M5 (1.0) | 91 | NM[a] |
| 17 | CE-2 + CAB-O-SIL M5 (0.5) | 37 | 5.2 |
| 18 | CE-2 + CAB-O-SIL M5 (0.25) | 8.7 | 1.8 |
| 19 | CE-2 + AEROSIL R972 (0.5) | 9.4 | 1.9 |
| 20 | CE-2 + CAB-O-SIL TS-720 (0.5) | 10 | 2.1 |
| CE-3 | OX-50 (1.94) | 3.8 | NM |
| TRANSBOND XT | — | 12 | 1.3 |

[a]NM—Not Measured

Water Uptake. Water Uptake was measured for Examples 2–3 and 5–6, Comparative Example 3, and the commercial product TRANSBOND XT orthodontic adhesive (3M Unitek) according to the Test Method described herein. Results in terms of percent increase in water uptake at Day 2 and Day 10 are reported in Table 4 and show (at Day 2) a significantly greater uptake of water by Examples 2–3 and 5–6 in comparison to the Comparative Example 3 or to the TRANSBOND XT. The enhanced water uptake can be attributed to the presence of substantially more hydrophilic polymers in the invention Examples 2–3 and 5–6. The hydrophilic nature of the adhesives used in the present invention facilitates fluoride transport and promotes the uptake of moisture or saliva so as to decrease the likelihood of bond failure (e.g., in the case of adhesive coated brackets bonded to moisture or saliva contaminated teeth).

TABLE 4

Water Uptake Value Results

| | Water Uptake Value (%) | |
| --- | --- | --- |
| Example | Day 2 | Day 10 |
| 2 | 0.61 | 1.41 |
| 3 | 0.95 | 2.04 |
| 5 | 1.15 | 2.43 |
| 6 | 0.79 | 1.74 |
| CE-3 | 0.30 | NM[a] |
| TRANSBOND XT | 0.20 | NM |

[a]NM—Not Measured

Adhesive/Bracket Flow-Out: The Adhesive/Bracket Flow-Out of Examples 12–15, 17–20, and Comparative Examples 1–3 was measured according to the Test Method described herein. Results are reported in Table 5 and show that the addition of low levels of various fumed silica materials to the adhesive compositions CE-1 and CE-2, which contained the fumed silica OX-50 at levels of 3.95% and 7.90%, respectively, afforded compositions (Examples 12–15 and 17–20) with rheological properties such that little or no flow-out was measured underneath the coated bracket. In contrast, significant flow-out was measured for Comparative Examples 1–3. Adhesive compositions that possess such rheological properties (i.e., minimal or no flow-out over time) are highly desirable for use as adhesives in adhesive-coated, packaged orthodontic appliances.

TABLE 5

Adhesive/Bracket Flow-Out Results

| Example | Fumed Silica Content (Weight %) | Time | Temp. | Flow-Out (mm) |
| --- | --- | --- | --- | --- |
| CE-1 | OX-50 (3.95) | 1 week | 40° C. | 0.48 |
| 12 | CE-1 + CAB-O-SIL M5 (0.5) | 1 week | 40° C. | 0 |
| 13 | CE-1 + CAB-O-SIL M5 (0.25) | 1 week | 40° C. | 0.30 |
| 14 | CE-1 + AEROSIL R972 (0.5) | 1 week | 40° C. | 0 |
| 15 | CE-1 + CAB-O-SIL TS-720 (0.5) | 1 week | 40° C. | 0 |
| CE-2 | OX-50 (7.90) | 1 week | 40° C. | 0.97 |
| 17 | CE-2 + CAB-O-SIL M5 (0.5) | 1 week | 40° C. | 0 |
| 18 | CE-2 + CAB-O-SIL M5 (0.25) | 1 week | 40° C. | 0.08 |
| 19 | CE-2 + AEROSIL R972 (0.5) | 1 week | 40° C. | 0 |
| 20 | CE-2 + CAB-O-SIL TS-720 (0.5) | 1 week | 40° C. | 0 |
| CE-3 | OX-50 (1.94) | 89 hours | Room Temp. | 1.27 |

Adhesive/Bracket Vertical Slip: The Adhesive/Bracket Vertical Slip of Examples 2 and 5, Comparative Examples 1–3 was measured according to the Test Method described herein. Results are reported in Table 6 and show that brackets coated with the inventive adhesive compositions (Examples 2 and 5 that contained a high surface area fumed silica material, i.e., CAB-O-SIL TS-720, with a surface area of about 105 to about 130 m$^2$/g) exhibited essentially no bracket slippage. In contrast, significant bracket slippage was measured for brackets coated with Comparative Examples 1–3 that contained only a fumed silica material of low surface area, i.e. OX-50 at levels of 3.95%, 7.90%, and 1.94%, respectively, with a surface area of about 35 m$^2$/g to about 65 m$^2$/g. It can be concluded from these results that the presence of a fumed silica material with relatively high surface area contributed to the enhanced rheological properties of the adhesive compositions. Adhesive compositions that possess such rheological properties (i.e., minimal or no slippage over time) are highly desirable for use as adhesives in adhesive-coated, packaged orthodontic appliances.

TABLE 6

Adhesive/Bracket Vertical Slip Results

| Example | Fumed Silica Content (Weight %) | Time | Temp. | Vertical Slip (mm) |
|---|---|---|---|---|
| 2 | CAB-O-SIL TS720 (1.25) AEROSIL R972 (0.62)[a] | 14 days | 50° C. | 0 |
| 5 | CAB-O-SIL TS720 (1.26) AEROSIL R972 (0.61)[a] | 11 days | 50° C. | 0 |
| CE-1 | OX-50 (3.95) | 3 days | 40° C. | 0.61 |
| CE-2 | OX-50 (7.90) | 3 days | 40° C. | 0.79 |
| CE-3 | OX-50 (1.94) | 26 hours | Room Temp. | 0.84 |

[a]From Filler A that contained about 1.6% by weight AEROSIL R972

Fluoride Release: The Fluoride Release of Examples 2–5 and 9 and the commercial product F2000 restorative (3M Company) was measured according to the Test Method described herein. Results in terms of micrograms of fluoride per gram of test sample at Days 1, 2, and 21 are reported in Table 7 and show cummulative fluoride release for Examples 2–5 and 9 and the F2000 restorative product. These results can be attributed to the presence of a fluoride releasing component(i.e., a FAS glass component) in both the inventive Example(s) and in F2000 restorative.

TABLE 7

Cumulative Fluoride Release Results

| Example | Fluoride Release (Micrograms Fluoride/Gram of Sample) | | |
|---|---|---|---|
| | Day 1 | Day 2 | Day 21 |
| 2 | 54 | 129 | NM[a] |
| 3 | 153 | NM[a] | NM[a] |
| 4 | 100 | 144 | 456 |
| 5 | 108 | NM[a] | 376 |
| 9 | 119 | 181 | 317 |
| F2000 | 123 | 154 | 394 |

[a]NM—Not Measured

Bond Strength for Moisture Tolerance: The Bond Strength under different moisture conditions for Example 1 and the commercial product TRANSBOND XT orthodonic adhesive (3M Unitek) was measured according to the Test Method described herein. Results in terms of Bond Strength under dry and moist conditions are reported in Table 8 and show, under dry conditions, comparable values for both Example 1 and for the TRANSBOND XT samples. However, under moist conditions, Example 1 showed significantly greater Bond Strength than the commercial product. This enhanced Bond Strength (in comparison to TRANSBOND XT) can be attributed to the presence of hydrophilic polymers in Example 1 of the present invention. This hydrophilic property of Example 1 promotes the uptake of moisture or saliva so as to decrease the likelihood of bond failure (e.g., in the case of adhesive coated brackets bonded to moisture or saliva contaminated teeth).

TABLE 8

Bond Strength Results

| Example | Bond Strength (MPa) | | |
|---|---|---|---|
| | Dry | Moist with Water | Moist with Saliva |
| 1 | 23 | 11 (48% of Dry) | 12 (56% of Dry) |
| TRANSBOND XT (Sample 1) | 22 | NM[a] | NM |
| TRANSBOND XT (Sample 2) | 19 | 6.5 (33% of Dry) | 1.2 (7% of Dry) |

[a]NM—Not Measured

Color Test: The qualification of initial and bleached color of Examples 2–5 and 8–9 were measured according to the Test Method described herein. Results in terms of a* values are reported in Table 9, and show acceptable loss of color (bleaching) following light curing of each of the Example adhesives containing photobleachable dye.

TABLE 9

Color (a*) Value Results

| Example | a* Value | |
|---|---|---|
| | Initial | After Curing |
| 2 | 34.28 | 0.42 |
| 3 | 43.09 | 0.91 |
| 4 | 41.70 | −1.28 |
| 5 | 39.79 | −1.62 |
| 8 | 51.30 | 2.46 |
| 9 | 46.40 | −1.54 |

White Light Stability: The quantification of color stability under white light conditions for Examples 2–3, 5 and 9 were measured according to the White Light Stability Method described herein. Results in terms of a* values are reported in Table 10. As expected, a gradual loss of color following exposure to fluorescent light occurred for each of the Example adhesives. However, after 5 minutes light exposure, the color a* values are still greater than 15, indicating that sufficient adhesive color is available for easy clean up of adhesive around a bracket that has been positioned on a tooth. Adhesive-coated brackets are typically removed from their package and ready for clean-up and final cure within about 5 minutes.

TABLE 10

Color (a*) Value Results

| Example | a* Value (Following Minutes of Light Exposure) | | | | |
|---|---|---|---|---|---|
| | 0 | 2 | 5 | 10 | 20 |
| 2 | 30.04 | 21.17 | 15.17 | 7.49 | 1.65 |
| 3 | 43.21 | 35.93 | 24.41 | 9.84 | 1.6 |
| 5 | 40.89 | 32.06 | 19.93 | 9.00 | 0.53 |
| 9 | 45.31 | 39.57 | 30.43 | 17.48 | 4.36 |

The complete disclosure of all patents, patent applications, and publications, and electronically available material cited herein are incorporated by reference. The foregoing detailed description and examples have been given for clarity of understanding only. No unnecessary limitations are to be understood therefrom. The invention is not limited to the exact details shown and described, for variations obvious to one skilled in the art will be included within the invention defined by the claims.

What is claimed is:

1. A packaged article comprising:
   an orthodontic appliance having a base for bonding the appliance to a tooth;
   an adhesive on the base of the appliance, the adhesive comprising a polymerizable component, a fluoride-releasing material, a hydrophilic component, a hardener, an acidic component, a base filler, and a filler comprising a fumed silica having a surface area of at least about 70 $m^2/g$, wherein the base filler is present at about 10% by weight to about 87% by weight, based on the total weight of the adhesive; and
   a container at least partially surrounding the orthodontic appliance having adhesive on the base thereof.

2. The article of claim 1 wherein the adhesive has a static yield stress at 28° C. of at least about 7000 dynes/$cm^2$.

3. The article of claim 1 wherein the adhesive has a flow-out value of no greater than about 0.4 millimeters after one week at 40° C.

4. The article of claim 1 further comprising a release substrate comprising a surface in contact with the adhesive.

5. The article of claim 4 wherein the surface of the release substrate comprises a number of pores, and no more than about 50% by weight of the adhesive is within the pores.

6. The article of claim 4 wherein the release substrate comprises a foam.

7. The article of claim 1 wherein the container provides a barrier to the transmission of light and/or water vapor.

8. The article of claim 1 wherein the fluoride-releasing material is a filler.

9. The article of claim 1 wherein the base filler is selected from the group consisting of quartz filler, fluoroaluminosilicate glass, and combinations thereof.

10. The article of claim 9 wherein the base filler is a quartz filler and the quartz filler comprises a silane treated surface.

11. The article of claim 1 wherein the fumed silica comprises a silane treated surface.

12. The article of claim 1 wherein the fumed silica comprises a silicone fluid treated fumed silica.

13. The article of claim 12 wherein the silicone treated fumed silica comprises a poly(dimethylsiloxane) fluid treated fumed silica.

14. The article of claim 1 wherein the fumed silica filler is present at about 0.1% by weight to about 50% by weight, based on the total weight of the adhesive.

15. The article of claim 14 wherein the base filler is present at about 45% by weight to about 85% by weight, based on the total weight of the adhesive, and the fumed silica filler is present at about 0.2% by weight to about 15% by weight, based on the total weight of the adhesive.

16. The article of claim 15 wherein the base filler is present at about 75% by weight to about 83% by weight, based on the total weight of the adhesive, and the fumed silica filler is present at about 0.5% by weight to about 3% by weight, based on the total weight of the adhesive.

17. The article of claim 1 wherein the fumed silica has a surface area of about 70 $m^2/g$ to about 1000 $m^2/g$.

18. The article of claim 17 wherein the fumed silica has a surface area of about 90 $m^2/g$ to about 500 $m^2/g$.

19. The article of claim 18 wherein the fumed silica has a surface area of about 100 $m^2/g$ to about 150 $m^2/g$.

20. The article of claim 1 wherein the fumed silica has an average aggregate length of about 0.01 micron to about 1 micron.

21. The article of claim 1 wherein the acidic component is a (meth)acryloyl substituted carboxyiic acid.

22. A packaged article comprising:
   an orthodontic appliance having a base for bonding the appliance to a tooth;
   an adhesive on the base of the appliance, the adhesive comprising a polymerizable component, a fluoride-releasing material, a hydrophilic component, a hardener, an acidic component, a base filler, a filler comprising a fumed silica having a surface area of at least about 70 $m^2/g$, and a photobleachable dye, wherein the base filler is present at about 10% by weight to about 87% by weight, based on the total weight of the adhesive, and wherein the adhesive has an initial color prior to exposure to actinic radiation and a final color subsequent to exposure to actinic radiation, the initial color being different than the final color; and
   a container at least partially surrounding the orthodontic appliance having adhesive on the base thereof.

23. The article of claim 22 wherein the acidic component is a (meth)acryloyl substituted carboxylic acid.

24. The article of claim 22 wherein the change in color from the initial color to the final color has a $\Delta E^*$ value greater than about 20.

25. The article of claim 22 wherein the hardener comprises a sensitizing compound, an electron donor, and an iodonium salt.

26. The article of claim 22 wherein the photobleachable dye is selected from the group consisting of Rose Bengal, Methylene Violet, Methylene Blue, Fluorescein, Eosin Yellow, Eosin Y, Ethyl Eosin, Eosin bluish, Eosin B, Erythrosin B, Erythrosin Yellowish Blend, Toluidine Blue, 4',5'-Dibromofluorescein, and combinations thereof.

27. The article of claim 22 wherein the final color is a tooth-like color or able to transmit the color of an underlying surface.

28. The article of claim 22 wherein the final color has a change in color, after aging for about 2 to about 4 days at about 37° C. under dark conditions, of no greater than about 16$\Delta E^*$.

29. A kit comprising:
   a packaged article comprising an orthodontic appliance having a base for bonding the appliance to a tooth, an adhesive on the base of the appliance, and a container at least partially surrounding the orthodontic appliance having adhesive on the base thereof, wherein the adhesive comprises a polymerizable component, a fluoride-releasing material, a hydrophilic component, a hardener, an acidic component, a base filler, and a filler comprising fumed silica having a surface area of at least about 70 $m^2/g$ wherein the base filler is present at about 10% by weight to about 87% by weight, based on the total weight of the adhesive; and
   instructions for using the orthodontic appliance.

30. The kit of claim 29 further comprising an etching composition.

31. A kit comprising:
   a packaged article comprising an orthodontic appliance having a base for bonding the appliance to a tooth, an adhesive on the base of the appliance, and a container at least partially surrounding the orthodontic appliance having adhesive on the base thereof, wherein the adhesive comprises a polymerizable component, a fluoride-releasing material, a hydrophilic component, a hardener, an acidic component, a base filler, a filler comprising a fumed silica having a surface area of at least about 70 $m^2/g$, and a photobleachable dye, wherein the base filler is present at about 10% by weight to about 87% by weight, based on the total weight of the adhesive, and wherein the adhesive has an initial color prior to exposure to actinic radiation and a final color subsequent to exposure to actinic radiation, the initial color being different than the final color; and instructions for using the orthodontic appliance.

32. A method of bonding an orthodontic appliance to a tooth comprising:

providing a packaged article comprising an orthodontic appliance having a base for bonding the appliance to a tooth, an adhesive on the base of the appliance, and a container at least partially surrounding the orthodontic appliance having adhesive on the base thereof, wherein the adhesive comprises a polymerizable component, a fluoride-releasing material, a hydrophilic component, a hardener, an acidic component, a base filler, and a filler comprising fumed silica having a surface area of at least about 70 $m^2/g$, wherein the base filler is present at about 10% by weight to about 87% by weight, based on the total weight of the adhesive;

removing the orthodontic appliance having adhesive on the base thereof from the container;

applying the base of the appliance to the tooth surface; and exposing the adhesive to actinic radiation.

33. The method of claim 32 further comprising applying an etching composition to the tooth surface before applying the base of the appliance to the tooth surface.

34. The method of claim 32 wherein the appliance bonds to the surface of a moistened tooth with an adhesion of at least about 7 MPa.

35. A method of bonding an orthodontic appliance to a tooth comprising:

providing a packaged article comprising an orthodontic appliance having a base for bonding the appliance to a tooth, an adhesive on the base of the appliance, and a container at least partially surrounding the orthodontic appliance having adhesive on the base thereof, wherein the adhesive comprises a polymerizable component, a fluoride-releasing material, a hydrophilic component, a hardener, an acidic component, a base filler, a filler comprising a fumed silica having a surface area of at least about 70 $m^2/g$, and a photobleachable dye, wherein the base filler is present at about 10% by weight to about 87% by weight, based on the total weight of the adhesive, and wherein the adhesive has an initial color prior to exposure to actinic radiation and a final color subsequent to exposure to actinic radiation, the initial color being different than the final color;

removing the orthodontic appliance having adhesive on the base thereof from the container;

applying the base of the appliance to the tooth surface; and exposing the adhesive to actinic radiation.

36. A packaged adhesive comprising:

an adhesive comprising a polymerizable component, a fluoride-releasing material, a hydrophilic component, a hardener, an acidic component, a base filler, and a filler comprising a fumed silica having a surface area of at least about 70 $m^2/g$, wherein the base filler is present at about 10% by weight to about 87% by weight, based on the total weight of the adhesive, and wherein the adhesive has a static yield stress at 28° C. of at least about 7000 dynes/$cm^2$ and a flow-out value of no greater than about 0.4 millimeters after one week at 40° C.; and a release substrate comprising a surface in contact with the adhesive.

37. A packaged adhesive comprising:

an adhesive comprising a polymerizable component, a fluoride-releasing material, a hydrophilic component, a hardener, an acidic component, a base filler, a filler comprising a fumed silica having a surface area of at least about 70 $m^2/g$, and a photobleachable dye, wherein the base filler is present at about 10% by weight to about 87% by weight, based on the total weight of the adhesive, and wherein the adhesive has an initial color prior to exposure to actinic radiation and a final color subsequent to exposure to actinic radiation, the initial color being different than the final color, and wherein the adhesive has a static yield stress at 28° C. of at least about 7000 dynes/$cm^2$; and a release substrate comprising a surface in contact with the adhesive.

* * * * *

UNITED STATES PATENT AND TRADEMARK OFFICE
CERTIFICATE OF CORRECTION

PATENT NO. : 6,960,079 B2  
DATED : November 1, 2005  
INVENTOR(S) : Brennan, Joan V.

It is certified that error appears in the above-identified patent and that said Letters Patent is hereby corrected as shown below:

Title page,  
Item [75], Inventors, "David K. Cinader" should read -- David. K. Cinader, Jr. --.

Column 10,  
Line 2, delete "3acryloxphenyl" and insert -- 3-acryloxyphenyl --.

Column 11,  
Line 48, delete "09/1489,612" and insert -- 09/489,612 --.  
Line 54, delete "Erythosin" and insert -- Erythrosin --; and delete "Erxythrosin" and insert -- Erythrosin --.

Column 14,  
Line 4, delete "Theological" and insert -- rheological --.

Column 15,  
Line 22, delete "prefexably" and insert -- preferably --.  
Line 26, delete "Chescr" and insert -- Chester --.  
Line 30, delete "2001" and insert -- 2002 --.

Column 16,  
Line 44, delete "MS" and insert -- M5 --.

Column 29,  
Line 67, delete "carboxyiic" and insert -- carboxylic --.

Signed and Sealed this

Fourteenth Day of March, 2006

JON W. DUDAS  
*Director of the United States Patent and Trademark Office*